(12) United States Patent
Takenaka et al.

(10) Patent No.: US 7,361,490 B2
(45) Date of Patent: *Apr. 22, 2008

(54) DNA ENCODING HYDANTOINASE, DNA ENCODING N-CARBAMYL-L-AMINO ACID HYDROLASE, RECOMBINANT DNA, TRANSFORMED CELL, METHOD OF PRODUCING PROTEIN AND METHOD OF PRODUCING OPTICALLY ACTIVE AMINO ACID

(75) Inventors: Yasuhiro Takenaka, Kanagawa (JP); Shunichi Suzuki, Kanagawa (JP); Norimasa Onishi, Kanagawa (JP); Kenzo Yokozeki, Kanagawa (JP)

(73) Assignee: AJinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/476,572

(22) Filed: Jun. 29, 2006

(65) Prior Publication Data

US 2006/0240532 A1   Oct. 26, 2006

Related U.S. Application Data

(60) Division of application No. 10/289,360, filed on Nov. 7, 2002, now Pat. No. 7,098,020, which is a continuation of application No. PCT/JP02/02173, filed on Mar. 8, 2002.

(30) Foreign Application Priority Data

Mar. 8, 2001  (JP)  ............................... 2001-065814
Sep. 27, 2001  (JP)  ............................... 2001-298619

(51) Int. Cl.
*C12P 13/22* (2006.01)
*C12P 13/04* (2006.01)
*C12N 9/86* (2006.01)

(52) U.S. Cl. ...................... 435/108; 435/106; 435/231

(58) Field of Classification Search ..................... None
See application file for complete search history.

(56) References Cited

U.S. PATENT DOCUMENTS

| | | | |
|---|---|---|---|
| 5,962,279 A * | 10/1999 | Nanba et al. ............... | 435/106 |
| 6,524,837 B1 * | 2/2003 | Arnold et al. ............... | 435/231 |
| 6,713,288 B1 | 3/2004 | Altenbuchner et al. | |
| 6,815,195 B2 | 11/2004 | Suzuki et al. | |
| 7,060,485 B2 | 6/2006 | Takenaka et al. | |
| 7,098,019 B2 | 8/2006 | Takenaka et al. | |
| 2006/0183892 A1 | 8/2006 | Takenaka et al. | |

FOREIGN PATENT DOCUMENTS

| | | |
|---|---|---|
| JP | 54-8749 | 1/1977 |
| JP | 54-84086 | 7/1979 |
| JP | 56-3034 | 7/1979 |
| JP | 63-24895 | 2/1988 |
| JP | 64-71476 | 3/1989 |
| JP | 3-19696 | 1/1991 |
| JP | 3-251176 | 11/1991 |
| JP | 4-271784 | 9/1992 |
| JP | 7-274985 | 10/1995 |
| WO | WO 00/58449 | 10/2000 |
| WO | WO 01/23582 A | 4/2001 |

OTHER PUBLICATIONS

May, O., et al. (1998) J. Biotech. 61, 1-13.*
Oliver May, et al., "Molecular Evolution of Hydantoinases", Biol. Chem., vol. 379, (Jun. 1998, pp. 743-747).
Anja Wiese, et al., "Hydantoin racemase from Arthrobacter aurescens DSM 3747: heterologous expression, purification and characterization", Journal of Biotechnology 80 (2000, pp. 217-230).
Oliver May, et al., "Substrate-dependent enantioselectivity of a novel hydantoinase from Arthrobacter aurescens DSM 3745: Purification and characterization as new member of cyclic amidases", Journal of Biotechnology 61(1998, pp. 1-13).
Ken Watabe, et al, "Identification and Sequencing of a Gene Encoding a Hydantoin Racemase from the Native Plasmid of Pseudomonas sp. Strain NS671", Journal of Bacteriology, (Jun. 1992, pp. 3461-3466).
Thomas Wagner, et al., "Production of L-methionine from D,L-5-(2-methylthioethyl) hydantoin by resting cells of a new mutant strain of Arthrobacter species DSM 7330", Journal of Biotechnology 46 (1996, pp. 63-68).
Kenzo Yokozeki, et al., "Mechanism of Asymmetric Production of L-Aromatic Amino Acids from the Corresponding Hydantoins by Flavobacterium sp.", Agric. Biol. Chem. 51 (3) (1987, pp. 737-746).

* cited by examiner

*Primary Examiner*—Elizabeth Slobodyansky
(74) *Attorney, Agent, or Firm*—Oblon, Spivak, McClelland, Maier & Neustadt, P.C.

(57) ABSTRACT

The present invention provides a method of producing optically active amino acids from 5-substituted hydantoin by isolating a hydantoinase gene and an N-carbamyl-L-amino acid hydrolase gene involved in an ability to convert 5-substituted hydantoin or N-carbamylamino acid into optically active amino acids from a microorganism of the genus *Microbacterium* having the above ability and by improving gene amplification and transcriptional and translational activities thereby preparing a recombinant wherein the amount of the desired enzymes produced is increased. The hydantoinase gene is, for example, a DNA encoding for a protein having a hydantoinase activity, which has the nucleotide sequence set forth in SEQ ID NO:1 in the Sequence. The N-carbamyl-L-amino acid hydrolase gene is, for example, a DNA encoding for a protein having an N-carbamyl-L-amino acid hydrolase activity, which has the nucleotide sequence set forth in SEQ ID NO:3 in the Sequence.

14 Claims, 1 Drawing Sheet

RESTRICTION ENZYME CLEAVAGE SITES:
E;*Eco*RI  K;*Kpn*I  B;*Bgl*II  P;*Pst*I  S;*Sac*I

SEQUENCE LISTING

```
<160> NUMBER OF SEQ ID NOS: 14

<210> SEQ ID NO 1
<211> LENGTH: 1380
<212> TYPE: DNA
<213> ORGANISM: Microbacterium liquefaciens
<220> FEATURE:
<221> NAME/KEY: CDS
<222> LOCATION: (1)..(1377)
<223> OTHER INFORMATION:

<400> SEQUENCE: 1 atg ttc gac gtc att gtg aag aac tgt cga gtg gtt tcc agt cag ggc      48
Met Phe Asp Val Ile Val Lys Asn Cys Arg Val Val Ser Ser Gln Gly
1               5                   10                  15 atc atc gaa gcc gac atc ctc gtg aag gac ggc cgg atc gcc gcc atc      96
Ile Ile Glu Ala Asp Ile Leu Val Lys Asp Gly Arg Ile Ala Ala Ile
            20                  25                  30 agc gag gag ccc ctc gag gcc gaa gcc gcc cgg acc atc gat gcc gca     144
Ser Glu Glu Pro Leu Glu Ala Glu Ala Ala Arg Thr Ile Asp Ala Ala
        35                  40                  45 ggc agg ttc gtg atg ccc ggt gtg gtc gat gaa cac gtg cac atc atc     192
Gly Arg Phe Val Met Pro Gly Val Val Asp Glu His Val His Ile Ile
    50                  55                  60 gac atg gat ctg aag gag gtc tac ggg cgg ttc gaa ctc gat tcc gag     240
Asp Met Asp Leu Lys Glu Val Tyr Gly Arg Phe Glu Leu Asp Ser Glu
65                  70                  75                  80 tcg gcg gcc gtc ggc ggt gtg acc acc atc atc gag atg ccg atc acg     288
Ser Ala Ala Val Gly Gly Val Thr Thr Ile Ile Glu Met Pro Ile Thr
                85                  90                  95 ttc ccg ccc acg acc acc ctg gag gcc ttc ctc gag aag aag aag cag     336
Phe Pro Pro Thr Thr Thr Leu Glu Ala Phe Leu Glu Lys Lys Lys Gln
            100                 105                 110 gga gag cag cga ctc aag gtc gac ttc gcg ctg tac ggc ggc gga gtg     384
Gly Glu Gln Arg Leu Lys Val Asp Phe Ala Leu Tyr Gly Gly Gly Val
        115                 120                 125 ccc gga aac ctg agc gag atc cgg aag atg cat gat gcc ggc gcc gtg     432
Pro Gly Asn Leu Ser Glu Ile Arg Lys Met His Asp Ala Gly Ala Val
    130                 135                 140 ggc ttc aag tcg atg atg gcg gcc tcc gtt ccc ggg atg ttc gaa gcc     480
Gly Phe Lys Ser Met Met Ala Ala Ser Val Pro Gly Met Phe Glu Ala
145                 150                 155                 160
```

```
gtc gac gac gga cag ctg ttc gag atc ttc cag gag atc gcg gcc tgc       528
Val Asp Asp Gly Gln Leu Phe Glu Ile Phe Gln Glu Ile Ala Ala Cys
                165                 170                 175 ggc tcg gtg atc gtg gtg cac gcc gag aac gag atg ctc atc cag acg       576
Gly Ser Val Ile Val Val His Ala Glu Asn Glu Met Leu Ile Gln Thr
            180                 185                 190 ctg cag aag cag ctc aag gcg gcc ggg cgc aag gac ctg gcg gcg tat       624
Leu Gln Lys Gln Leu Lys Ala Ala Gly Arg Lys Asp Leu Ala Ala Tyr
        195                 200                 205 gag gcg tcc cag ccg gtc ttc cag gag aac gag gcg atc cag cgc gcg       672
Glu Ala Ser Gln Pro Val Phe Gln Glu Asn Glu Ala Ile Gln Arg Ala
    210                 215                 220 ctg ctc ctg cag aag gag gcg ggc tgc cga ctc atc gtc gtt cac gtg       720
Leu Leu Leu Gln Lys Glu Ala Gly Cys Arg Leu Ile Val Val His Val
225                 230                 235                 240 agc aac ccc ggc ggc gtg gag ttg atc cac aag gcg cag tcg gag ggt       768
Ser Asn Pro Gly Gly Val Glu Leu Ile His Lys Ala Gln Ser Glu Gly
                245                 250                 255 cag gac gtg cac tgc gag tca ggc cct cag tac ctc aac ctc aca atg       816
Gln Asp Val His Cys Glu Ser Gly Pro Gln Tyr Leu Asn Leu Thr Met
            260                 265                 270 gat gac gcc gag aag gtc ggc ccg tac atg aag atc gcc ccg ccg gtc       864
Asp Asp Ala Glu Lys Val Gly Pro Tyr Met Lys Ile Ala Pro Pro Val
        275                 280                 285 cgt tcg gcc gag ctg aac gcc gtc ctc tgg gag cag ctc gag aag ggg       912
Arg Ser Ala Glu Leu Asn Ala Val Leu Trp Glu Gln Leu Glu Lys Gly
    290                 295                 300 tac atc gac acg ctc gga tcg gat cac ggt ggg cac ccc gtc gag aac       960
Tyr Ile Asp Thr Leu Gly Ser Asp His Gly Gly His Pro Val Glu Asn
305                 310                 315                 320 aag gag ggc ggc tgg gac gac atc tgg acg gcc agc aac ggt gcg ctg      1008
Lys Glu Gly Gly Trp Asp Asp Ile Trp Thr Ala Ser Asn Gly Ala Leu
                325                 330                 335 gga ctg gag acg tcg ctg ccg atg atg ctg acc aac ggc gtc aac aag      1056
Gly Leu Glu Thr Ser Leu Pro Met Met Leu Thr Asn Gly Val Asn Lys
            340                 345                 350 ggc cgc gtc tcg ctg gag cga ctg gtc gag gtg atg tgc gag aac ccg      1104
Gly Arg Val Ser Leu Glu Arg Leu Val Glu Val Met Cys Glu Asn Pro
        355                 360                 365 gcg aag ctc ttc ggg atc tat ccg cag aag ggc acg ctc cag gtc ggc      1152
Ala Lys Leu Phe Gly Ile Tyr Pro Gln Lys Gly Thr Leu Gln Val Gly
    370                 375                 380 tcg gac gcc gat ctc ctc atc ctc gat ctc gag atc gag gac agg aag      1200
Ser Asp Ala Asp Leu Leu Ile Leu Asp Leu Glu Ile Glu Asp Arg Lys
385                 390                 395                 400 gtg gat gct tcg cag ttc cgc tcg ctc ctg cac tac agt cca ttc gat      1248
Val Asp Ala Ser Gln Phe Arg Ser Leu Leu His Tyr Ser Pro Phe Asp
                405                 410                 415 gga cgg ccg gtc acc ggc gcg ccc gtc ctc acg atg atc cgt gga aca      1296
Gly Arg Pro Val Thr Gly Ala Pro Val Leu Thr Met Ile Arg Gly Thr
            420                 425                 430 gtc gtc gcc cag gac gga gag atc ctc gtc gac cag ggg ttc ggg cag      1344
Val Val Ala Gln Asp Gly Glu Ile Leu Val Asp Gln Gly Phe Gly Gln
        435                 440                 445 ttc gtg acc cgg cgc gac agc gag gtg tcg tcg tga                      1380
Phe Val Thr Arg Arg Asp Ser Glu Val Ser Ser
    450                 455

<210> SEQ ID NO 2
```

```
<211> LENGTH: 459
<212> TYPE: PRT
<213> ORGANISM: Microbacterium liquefaciens

<400> SEQUENCE: 2

Met Phe Asp Val Ile Val Lys Asn Cys Arg Val Val Ser Ser Gln Gly
1               5                   10                  15

Ile Ile Glu Ala Asp Ile Leu Val Lys Asp Gly Arg Ile Ala Ala Ile
            20                  25                  30

Ser Glu Glu Pro Leu Glu Ala Glu Ala Ala Arg Thr Ile Asp Ala Ala
        35                  40                  45

Gly Arg Phe Val Met Pro Val Val Asp Glu His Val His Ile Ile
50                  55                  60

Asp Met Asp Leu Lys Glu Val Tyr Gly Arg Phe Glu Leu Asp Ser Glu
65                  70                  75                  80

Ser Ala Ala Val Gly Gly Val Thr Thr Ile Ile Glu Met Pro Ile Thr
                85                  90                  95

Phe Pro Pro Thr Thr Thr Leu Glu Ala Phe Leu Glu Lys Lys Lys Gln
            100                 105                 110

Gly Glu Gln Arg Leu Lys Val Asp Phe Ala Leu Tyr Gly Gly Val
        115                 120                 125

Pro Gly Asn Leu Ser Glu Ile Arg Lys Met His Asp Ala Gly Ala Val
    130                 135                 140

Gly Phe Lys Ser Met Met Ala Ala Ser Val Pro Gly Met Phe Glu Ala
145                 150                 155                 160

Val Asp Asp Gly Gln Leu Phe Glu Ile Phe Gln Glu Ile Ala Ala Cys
                165                 170                 175

Gly Ser Val Ile Val His Ala Glu Asn Glu Met Leu Ile Gln Thr
            180                 185                 190

Leu Gln Lys Gln Leu Lys Ala Ala Gly Arg Lys Asp Leu Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Val His Val
225                 230                 235                 240

Ser Asn Pro Gly Gly Val Glu Leu Ile His Lys Ala Gln Ser Glu Gly
                245                 250                 255

Gln Asp Val His Cys Glu Ser Gly Pro Gln Tyr Leu Asn Leu Thr Met
            260                 265                 270

Asp Asp Ala Glu Lys Val Gly Pro Tyr Met Lys Ile Ala Pro Pro Val
        275                 280                 285

Arg Ser Ala Glu Leu Asn Ala Val Leu Trp Glu Gln Leu Glu Lys Gly
    290                 295                 300

Tyr Ile Asp Thr Leu Gly Ser Asp His Gly His Pro Val Glu Asn
305                 310                 315                 320

Lys Glu Gly Gly Trp Asp Asp Ile Trp Thr Ala Ser Asn Gly Ala Leu
                325                 330                 335

Gly Leu Glu Thr Ser Leu Pro Met Met Leu Thr Asn Gly Val Asn Lys
            340                 345                 350

Gly Arg Val Ser Leu Glu Arg Leu Val Glu Val Met Cys Glu Asn Pro
        355                 360                 365

Ala Lys Leu Phe Gly Ile Tyr Pro Gln Lys Gly Thr Leu Gln Val Gly
    370                 375                 380

Ser Asp Ala Asp Leu Leu Ile Leu Asp Leu Glu Ile Glu Asp Arg Lys
```

```
                385                 390                 395                 400
Val Asp Ala Ser Gln Phe Arg Ser Leu Leu His Tyr Ser Pro Phe Asp
                    405                 410                 415

Gly Arg Pro Val Thr Gly Ala Pro Val Leu Thr Met Ile Arg Gly Thr
                420                 425                 430

Val Val Ala Gln Asp Gly Glu Ile Leu Val Asp Gln Gly Phe Gly Gln
            435                 440                 445

Phe Val Thr Arg Arg Asp Ser Glu Val Ser Ser
        450                 455

<210> SEQ ID NO 3
<211> LENGTH: 1239
<212> TYPE: DNA
<213> ORGANISM: Microbacterium liquefaciens
<220> FEATURE:
<221> NAME/KEY: CDS
<222> LOCATION: (1)..(1239)
<223> OTHER INFORMATION:

<400> SEQUENCE: 3 gtg acg ctg cag cag gcg cgg gcc gat cgc atc gag gag gag ctc tgg      48
Val Thr Leu Gln Gln Ala Arg Ala Asp Arg Ile Glu Glu Glu Leu Trp
1               5                  10                  15 act ctc tcc cgc ttc tcg gtc gaa ggg ccc ggc gtg aca cgt ctc acg      96
Thr Leu Ser Arg Phe Ser Val Glu Gly Pro Gly Val Thr Arg Leu Thr
            20                  25                  30 tac act ccg gag cac gcc gcc gcg cga gag gtg atc gtc gcc gcc atg    144
Tyr Thr Pro Glu His Ala Ala Ala Arg Glu Val Ile Val Ala Ala Met
        35                  40                  45 cag cgg acg ggg ctg agc gtc cac gag gac gct ctc ggc aac atc atc    192
Gln Arg Thr Gly Leu Ser Val His Glu Asp Ala Leu Gly Asn Ile Ile
    50                  55                  60 ggt cgg cgt gag ggg agc gac ccc gct ctg ccg gcg atc gcc ttc ggc    240
Gly Arg Arg Glu Gly Ser Asp Pro Ala Leu Pro Ala Ile Ala Phe Gly
65                  70                  75                  80 tcg cac ttc gac tcg gtc cgc aac ggc ggg atg ttc gac ggc acc gcg    288
Ser His Phe Asp Ser Val Arg Asn Gly Gly Met Phe Asp Gly Thr Ala
                85                  90                  95 ggc gtg gtg tgc gcg ctc gag gct gcg agg gtg ctg cag gag agc gga    336
Gly Val Val Cys Ala Leu Glu Ala Ala Arg Val Leu Gln Glu Ser Gly
            100                 105                 110 tat gtg aac cgt cat cct ctc gag gtc atc gcg atc gtc gaa gag gag    384
Tyr Val Asn Arg His Pro Leu Glu Val Ile Ala Ile Val Glu Glu Glu
        115                 120                 125 ggc acc cgc ttc agc agc ggc atg ctg ggc ggt cgc gcg atc gcg ggg    432
Gly Thr Arg Phe Ser Ser Gly Met Leu Gly Gly Arg Ala Ile Ala Gly
    130                 135                 140 ctc gtg tcc gac gcc gat ctg gac acc ctg gtg gac gaa gac ggc gtg    480
Leu Val Ser Asp Ala Asp Leu Asp Thr Leu Val Asp Glu Asp Gly Val
145                 150                 155                 160 acg gtg cgc gag gcg gcc acg gcc ttc ggg ctg gaa ccg ggt gag ctg    528
Thr Val Arg Glu Ala Ala Thr Ala Phe Gly Leu Glu Pro Gly Glu Leu
                165                 170                 175 cgg acg gcg gcc cgt acg agg gat gac ctt cgc gcc ttc atc gag ttg    576
Arg Thr Ala Ala Arg Thr Arg Asp Asp Leu Arg Ala Phe Ile Glu Leu
            180                 185                 190 cac atc gag cag ggg ccg atc ctc gag cag gag aag gtg gag atc ggc    624
His Ile Glu Gln Gly Pro Ile Leu Glu Gln Glu Lys Val Glu Ile Gly
        195                 200                 205 gtc gtg acg ggg atc gtc ggt gtc cgc gcc ttc cgg atc acg gtg gag    672
```

-continued

```
        Val Val Thr Gly Ile Val Gly Val Arg Ala Phe Arg Ile Thr Val Glu
            210                 215                 220 ggc agg agc gac cac gcc ggg acg acc ccc atg cac ctg cgg cag gac        720
Gly Arg Ser Asp His Ala Gly Thr Thr Pro Met His Leu Arg Gln Asp
225                 230                 235                 240 gcg ctg gtg ccg gcg gcg ctc atg gtg cga gag atc aat cgg ttc gtc        768
Ala Leu Val Pro Ala Ala Leu Met Val Arg Glu Ile Asn Arg Phe Val
                245                 250                 255 aac gag atc gcg gac ggc acg gtg gcg acc gtc ggc cac ctc acg gtg        816
Asn Glu Ile Ala Asp Gly Thr Val Ala Thr Val Gly His Leu Thr Val
            260                 265                 270 acc cct ggt ggg ctc aac cag gtt ccc ggg ggc gtc gag ttc acg ctc        864
Thr Pro Gly Gly Leu Asn Gln Val Pro Gly Gly Val Glu Phe Thr Leu
        275                 280                 285 gat ctg cga tcg ccc cac gag gag tcg atc cgg ctc ctg gtc gac agg        912
Asp Leu Arg Ser Pro His Glu Glu Ser Ile Arg Leu Leu Val Asp Arg
    290                 295                 300 atc gag gcg atg gtg gca gaa gtc gcc gcc gcg gcc gga gtc gag gcc        960
Ile Glu Ala Met Val Ala Glu Val Ala Ala Ala Ala Gly Val Glu Ala
305                 310                 315                 320 gcg gtg aac ggg ttc ttc gcg ctc agc cct gtc ggt ctg tct ccg gtg       1008
Ala Val Asn Gly Phe Phe Ala Leu Ser Pro Val Gly Leu Ser Pro Val
                325                 330                 335 gtc gtg gat cgc gtg cgc gac gcg gcg tcc gaa ctc ggc ttc acc cat       1056
Val Val Asp Arg Val Arg Asp Ala Ala Ser Glu Leu Gly Phe Thr His
            340                 345                 350 cgc gac atc acg agc ggg gca ggg cac gac tcg atg ttc atc gcc cag       1104
Arg Asp Ile Thr Ser Gly Ala Gly His Asp Ser Met Phe Ile Ala Gln
        355                 360                 365 atc acc gac gtc gga atg gtg ttc gtc ccc agc cgc gcc ggg cga agc       1152
Ile Thr Asp Val Gly Met Val Phe Val Pro Ser Arg Ala Gly Arg Ser
    370                 375                 380 cat gtg ccg gag gaa tgg tcc gat ttc gac gat ctg cgg aag ggg acg       1200
His Val Pro Glu Glu Trp Ser Asp Phe Asp Asp Leu Arg Lys Gly Thr
385                 390                 395                 400 gat gtg gtc ctt cac gtc gtg acg gcg ctt gac cgg tga                   1239
Asp Val Val Leu His Val Val Thr Ala Leu Asp Arg
                405                 410
```

<210> SEQ ID NO 4
<211> LENGTH: 412
<212> TYPE: PRT
<213> ORGANISM: Microbacterium liquefaciens

<400> SEQUENCE: 4

```
Val Thr Leu Gln Gln Ala Arg Ala Asp Arg Ile Glu Glu Glu Leu Trp
1               5                   10                  15

Thr Leu Ser Arg Phe Ser Val Glu Gly Pro Gly Val Thr Arg Leu Thr
            20                  25                  30

Tyr Thr Pro Glu His Ala Ala Ala Arg Glu Val Ile Val Ala Ala Met
        35                  40                  45

Gln Arg Thr Gly Leu Ser Val His Glu Asp Ala Leu Gly Asn Ile Ile
    50                  55                  60

Gly Arg Arg Glu Gly Ser Asp Pro Ala Leu Pro Ala Ile Ala Phe Gly
65                  70                  75                  80

Ser His Phe Asp Ser Val Arg Asn Gly Gly Met Phe Asp Gly Thr Ala
                85                  90                  95

Gly Val Val Cys Ala Leu Glu Ala Ala Arg Val Leu Gln Glu Ser Gly
            100                 105                 110
```

```
Tyr Val Asn Arg His Pro Leu Glu Val Ile Ala Ile Val Glu Glu Glu
            115                 120                 125

Gly Thr Arg Phe Ser Ser Gly Met Leu Gly Gly Arg Ala Ile Ala Gly
        130                 135                 140

Leu Val Ser Asp Ala Asp Leu Asp Thr Leu Val Asp Glu Asp Gly Val
145                 150                 155                 160

Thr Val Arg Glu Ala Ala Thr Ala Phe Gly Leu Glu Pro Gly Glu Leu
                165                 170                 175

Arg Thr Ala Ala Arg Thr Arg Asp Asp Leu Arg Ala Phe Ile Glu Leu
            180                 185                 190

His Ile Glu Gln Gly Pro Ile Leu Glu Gln Glu Lys Val Glu Ile Gly
        195                 200                 205

Val Val Thr Gly Ile Val Gly Val Arg Ala Phe Arg Ile Thr Val Glu
    210                 215                 220

Gly Arg Ser Asp His Ala Gly Thr Thr Pro Met His Leu Arg Gln Asp
225                 230                 235                 240

Ala Leu Val Pro Ala Ala Leu Met Val Arg Glu Ile Asn Arg Phe Val
                245                 250                 255

Asn Glu Ile Ala Asp Gly Thr Val Ala Thr Val Gly His Leu Thr Val
            260                 265                 270

Thr Pro Gly Gly Leu Asn Gln Val Pro Gly Gly Val Glu Phe Thr Leu
        275                 280                 285

Asp Leu Arg Ser Pro His Glu Glu Ser Ile Arg Leu Leu Val Asp Arg
    290                 295                 300

Ile Glu Ala Met Val Ala Glu Val Ala Ala Ala Gly Val Glu Ala
305                 310                 315                 320

Ala Val Asn Gly Phe Phe Ala Leu Ser Pro Val Gly Leu Ser Pro Val
                325                 330                 335

Val Val Asp Arg Val Arg Asp Ala Ala Ser Glu Leu Gly Phe Thr His
            340                 345                 350

Arg Asp Ile Thr Ser Gly Ala Gly His Asp Ser Met Phe Ile Ala Gln
        355                 360                 365

Ile Thr Asp Val Gly Met Val Phe Val Pro Ser Arg Ala Gly Arg Ser
    370                 375                 380

His Val Pro Glu Glu Trp Ser Asp Phe Asp Asp Leu Arg Lys Gly Thr
385                 390                 395                 400

Asp Val Val Leu His Val Val Thr Ala Leu Asp Arg
                405                 410

<210> SEQ ID NO 5
<211> LENGTH: 3343
<212> TYPE: DNA
<213> ORGANISM: Microbacterium liquefaciens

<400> SEQUENCE: 5
atgagaatcc atgtcatcaa tcccaacagc tcggtggatc tcaccgatgc ggtggccgag      60
gcggcgcgaa gtgtggtgtc accgggaacc accatcaccg cggtcaaccc ttcgaagggc    120
cccacggtca tcgagggcag ttacgacgag gtgctggcca cgtatcacct cgtcgaagag    180
gtccgccgcg cggagcgcga agaccgaccg gacgcctacg tcatcgcctg tttcggcgat    240
ccaggtctcg acgccgtcag ggagctcacc gacaggcccg tggtcggaat cgccgaggcg    300
gcgatccaga tgacgagctt cgtcgccgcg agcttctcca tcgtgagcat cctcccgcgc    360
gtgcgcaagc atctgcacga gctggtgcac cgggcggggg caacggatcg actcgccctca   420
```

-continued

```
ctcaagcttc cggatctcgg agtgctcgca ttccacgagg acgaggcagc ggcgttcgag    480
accctccggc gcgtggcagg tgaggcggtg cgcgaggacg gcgcggagtc gatcgtgctc    540
ggctgcgcgg gcatggccgg attcgccaga cagctgagtg aagagctcgg cgtccccgtc    600
atcgacgcgg tcgaggcagc ctgccgcgtc gcggagagcc tcgtcgccct ggggtaccgc    660
accagcaagg cgaacaccta ccaagcaccc accgagaagc agtacctcta acgagaagga    720
gcgatgtcat gttcgacgtc attgtgaaga actgtcgagt ggtttccagt cagggcatca    780
tcgaagccga catcctcgtg aaggacggcc ggatcgccgc catcagcgag agcccctcg    840
aggccgaagc cgcccggacc atcgatgccg caggcaggtt cgtgatgccc ggtgtggtcg    900
atgaacacgt gcacatcatc gacatggatc tgaaggagg ctacgggcgg ttcgaactcg    960
attccgagtc ggcggccgtc ggcggtgtga ccaccatcat cgagatgccg atcacgttcc   1020
cgcccacgac caccctggag gccttcctcg agaagaagaa gcaggagag cagcgactca   1080
aggtcgactt cgcgctgtac ggcggcgag tgcccggaaa cctgagcgag atccggaaga   1140
tgcatgatgc cggcgccgtg ggcttcaagt cgatgatggc ggcctccgtt cccgggatgt   1200
tcgaagccgt cgacgacgga cagctgttcg agatcttcca ggagatcgcg gcctgcggct   1260
cggtgatcgt ggtgcacgcc gagaacgaga tgctcatcca cgactgcag aagcagctca   1320
aggcggccgg gcgcaaggac ctggcggcgt atgaggcgtc ccagccggtc ttccaggaga   1380
acgaggcgat ccagcgcgcg ctgctcctgc agaaggaggc gggctgccga ctcatcgtcg   1440
ttcacgtgag caaccccggc ggcgtggagt tgatccacaa ggcgcagtcg gagggtcagg   1500
acgtgcactg cgagtcaggc cctcagtacc tcaacctcac aatggatgac gccgagaagg   1560
tcggcccgta catgaagatc gccccgccgg tccgttcggc cgagctgaac gccgtcctct   1620
gggagcagct cgagaagggg tacatcgaca cgctcggatc ggatcacggt gggcaccccg   1680
tcgagaacaa ggagggcggc tgggacgaca tctggacggc cagcaacggt gcgctgggac   1740
tggagacgtc gctgccgatg atgctgacca acggcgtcaa caagggccgc gtctcgctgg   1800
agcgactggt cgaggtgatg tgcgagaacc cggcgaagct cttcgggatc tatccgcaga   1860
agggcacgct ccaggtcggc tcggacgccg atctcctcat cctcgatctc gagatcgagg   1920
acaggaaggt ggatgcttcg cagttccgct cgctcctgca ctacagtcca ttcgatggac   1980
ggccggtcac cggcgcgccc gtcctcacga tgatccgtgg aacagtcgtc gcccaggacg   2040
gagagatcct cgtcgaccag gggttcgggc agttcgtgac ccggcgcgac agcgaggtgt   2100
cgtcgtgacg ctgcagcagg cgcgggccga tcgcatcgag gaggagctct ggactctctc   2160
ccgcttctcg gtcgaagggc ccggcgtgac acgtctcacg tacactccgg agcacgccgc   2220
cgcgcgagag gtgatcgtcg ccgccatgca gcggacgggg ctgagcgtcc acgaggacgc   2280
tctcggcaac atcatcggtc ggcgtgaggg gagcgacccc gctctgccgg cgatcgcctt   2340
cggctcgcac ttcgactcgg tccgcaacgg cgggatgttc gacggcaccg cgggcgtggt   2400
gtgcgcgctc gaggctgcga gggtgctgca ggagagcgga tatgtgaacc gtcatcctct   2460
cgaggtcatc gcgatcgtcg aagaggaggg cacccgcttc agcagcggca tgctgggcgg   2520
tcgcgcgatc gcggggctcg tgtccgacgc cgatctggac accctggtgg acgaagacgg   2580
cgtgacggtg cgcgaggcgg ccacggcctt cgggctggaa ccgggtgagc tgcggacggc   2640
ggcccgtacg agggatgacc ttcgcgcctt catcgagttg cacatcgagc aggggccgat   2700
cctcgagcag gagaaggtgg agatcggcgt cgtgacgggg atcgtcggtg tccgcgcctt   2760
```

```
ccggatcacg gtggagggca ggagcgacca cgccggacg accccccatgc acctgcggca    2820 ggacgcgctg gtgccggcgg cgctcatggt gcgagagatc aatcggttcg tcaacgagat    2880
cgcggacggc acggtggcga ccgtcggcca cctcacggtg accccctggtg ggctcaacca    2940 ggttcccggg ggcgtcgagt tcacgctcga tctgcgatcg ccccacgagg agtcgatccg    3000
gctcctggtc gacaggatcg aggcgatggt ggcagaagtc gccgccgcgg ccggagtcga    3060
ggccgcggtg aacgggttct tcgcgctcag ccctgtcggt ctgtctccgg tggtcgtgga    3120
tcgcgtgcgc gacgcggcgt ccgaactcgg cttcacccat cgcgacatca cgagcggggc    3180
agggcacgac tcgatgttca tcgcccagat caccgacgtc ggaatggtgt tcgtccccag    3240
ccgcgccggg cgaagccatg tgccggagga atggtccgat ttcgacgatc tgcggaaggg    3300
gacggatgtg gtccttcacg tcgtgacggc gcttgaccgg tga                     3343
```

<210> SEQ ID NO 6
<211> LENGTH: 236
<212> TYPE: PRT
<213> ORGANISM: Microbacterium liquefaciens

<400> SEQUENCE: 6

```
Met Arg Ile His Val Ile Asn Pro Asn Ser Val Asp Leu Thr Asp
1               5                   10                  15

Ala Val Ala Glu Ala Ala Arg Ser Val Val Ser Pro Gly Thr Thr Ile
                20                  25                  30

Thr Ala Val Asn Pro Ser Lys Gly Pro Thr Val Ile Glu Gly Ser Tyr
            35                  40                  45

Asp Glu Val Leu Ala Thr Tyr His Leu Val Glu Glu Val Arg Arg Ala
        50                  55                  60

Glu Arg Glu Asp Arg Pro Asp Ala Tyr Val Ile Ala Cys Phe Gly Asp
65                  70                  75                  80

Pro Gly Leu Asp Ala Val Arg Glu Leu Thr Asp Arg Pro Val Val Gly
                85                  90                  95

Ile Ala Glu Ala Ala Ile Gln Met Thr Ser Phe Val Ala Ala Ser Phe
            100                 105                 110

Ser Ile Val Ser Ile Leu Pro Arg Val Arg Lys His Leu His Glu Leu
        115                 120                 125

Val His Arg Ala Gly Ala Thr Asp Arg Leu Ala Ser Leu Lys Leu Pro
    130                 135                 140

Asp Leu Gly Val Leu Ala Phe His Glu Asp Glu Ala Ala Ala Phe Glu
145                 150                 155                 160

Thr Leu Arg Arg Val Ala Gly Glu Ala Val Arg Glu Asp Gly Ala Glu
                165                 170                 175

Ser Ile Val Leu Gly Cys Ala Gly Met Ala Gly Phe Ala Arg Gln Leu
            180                 185                 190

Ser Glu Glu Leu Gly Val Pro Val Ile Asp Ala Val Glu Ala Ala Cys
        195                 200                 205

Arg Val Ala Glu Ser Leu Val Ala Leu Gly Tyr Arg Thr Ser Lys Ala
    210                 215                 220

Asn Thr Tyr Gln Ala Pro Thr Glu Lys Gln Tyr Leu
225                 230                 235
```

<210> SEQ ID NO 7
<211> LENGTH: 32
<212> TYPE: DNA
<213> ORGANISM: Artificial Sequence
<220> FEATURE:

<223> OTHER INFORMATION: Synthetic DNA

<400> SEQUENCE: 7
ctgcagcgtc tggatgagca tctcgttctc gg                32

<210> SEQ ID NO 8
<211> LENGTH: 29
<212> TYPE: DNA
<213> ORGANISM: Artificial Sequence
<220> FEATURE:
<223> OTHER INFORMATION: Synthetic DNA

<400> SEQUENCE: 8
atcgatgccg caggcaggtt cgtgatgcc                29

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
acgccgagaa cgagatgctc atccagacgc                30

<210> SEQ ID NO 10
<211> LENGTH: 23
<212> TYPE: DNA
<213> ORGANISM: Artificial Sequence
<220> FEATURE:
<223> OTHER INFORMATION: Synthetic DNA

<400> SEQUENCE: 10
ggtcacgaac tgcccgaacc cct                23

<210> SEQ ID NO 11
<211> LENGTH: 32
<212> TYPE: DNA
<213> ORGANISM: Artificial Sequence
<220> FEATURE:
<223> OTHER INFORMATION: Synthetic DNA

<400> SEQUENCE: 11
cgcgaattcc gagaaggagc gctgtcatgt tc                32

<210> SEQ ID NO 12
<211> LENGTH: 30
<212> TYPE: DNA
<213> ORGANISM: Artificial Sequence
<220> FEATURE:
<223> OTHER INFORMATION: Synthetic DNA

<400> SEQUENCE: 12
cgcggatccg atgcgatcgg cccgcgcctg                30

<210> SEQ ID NO 13
<211> LENGTH: 37
<212> TYPE: DNA
<213> ORGANISM: Artificial Sequence
<220> FEATURE:
<223> OTHER INFORMATION: Synthetic DNA

<400> SEQUENCE: 13
cgcgaattcg cgagagggag gtgtcgtcat gacgctg                37

```
<210> SEQ ID NO 14
<211> LENGTH: 36
<212> TYPE: DNA
<213> ORGANISM: Artificial Sequence
<220> FEATURE:
<223> OTHER INFORMATION: Synthetic DNA

<400> SEQUENCE: 14
cgcggatcca acgtcaccgg tcaagcgccg tcacga                                36
```

DNA ENCODING HYDANTOINASE, DNA ENCODING N-CARBAMYL-L-AMINO ACID HYDROLASE, RECOMBINANT DNA, TRANSFORMED CELL, METHOD OF PRODUCING PROTEIN AND METHOD OF PRODUCING OPTICALLY ACTIVE AMINO ACID

This application is a divisional of U.S. application Ser. No. 10/289,360, filed on Nov. 7, 2002 now U.S. Pat. No. 7,098,020, which is a continuation of PCT/JP02/02173, filed on Mar. 8, 2002, which claims priority to JP 2001-065814, filed on Mar. 8, 2001, and JP 2001-298619, filed on Sep. 27, 2001.

TECHNICAL FIELD

The present invention relates to a DNA encoding hydantoinase and a DNA encoding N-carbamyl-L-amino acid hydrolase and in particular to a DNA encoding hydantoinase, a DNA encoding N-carbamyl-L-amino acid hydrolase, a recombinant DNA, a transformed cell, a method of producing a protein and a method of producing optically active amino acids, which can be used preferably in production of optically active amino acids represented by L-tyrosine.

BACKGROUND ART

As one of methods for producing amino acids by use of an enzyme, a method of asymmetric decomposition of chemically inexpensively synthesized 5-substituted hydantoin compounds as the starting material into optically active amino acids is known. This method of producing optically active amino acids from 5-substituted hydantoin compounds is important for production of pharmaceutical preparations, products in chemical industry, food additives etc.

In this method of producing amino acids from 5-substituted hydantoin compounds, the following enzymes (1) and (2) are necessary.

(1) An enzyme (hydantoinase) of catalyzing the reaction of forming N-carbamylamino acid by acting on a 5-substituted hydantoin compound to hydrolyze the compound.

(2) An enzyme (N-carbamylamino acid hydrolase) of catalyzing the reaction of forming an optically active amino acid by acting on the formed N-carbamylamino acid to hydrolyze the compound.

For producing optically active amino acids from 5-substituted hydantoin compounds, (1) hydantoinase and/or (2) N-carbamylamino acid hydrolase must be an optically selective enzyme, and a method of using a microbial enzyme system and a method of combining a microbial enzyme system with a chemical reaction system have been known.

For example, the known method of producing D-amino acids by a D-amino acid-producing microorganism or by enzyme-containing materials produced by the microorganism includes a method of using a microorganism of the genus *Pseudomonas* (Japanese Patent Application Publication No. 56-003034), a method of using a microorganism of the genus *Agrobacterium* (Japanese Patent Application Laid-Open No. 03-019696) etc. In these D-amino acid-producing microorganisms, their hydantoinase activity is generally often specific to D-5-substituted hydantoin, and when DL-5-substituted hydantoin is used as the starting material, only the D-hydantoin is hydrolyzed to form N-carbamyl-D-amino acid, which is further hydrolyzed to finally give D-amino acid only, as shown in the following reaction scheme (I).

D-Amino Acid-Producing Microorganism

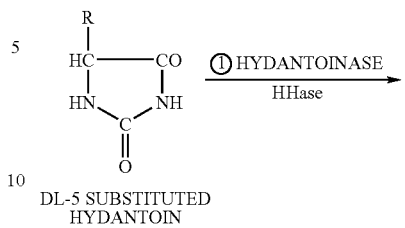

DL-5 SUBSTITUTED HYDANTOIN

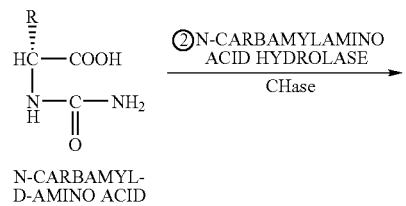

N-CARBAMYL-D-AMINO ACID

D-AMINO ACID (I)

As the method of producing L-amino acids by an L-amino acid-producing microorganism or by enzyme-containing materials produced by the microorganism, there are reports on a method of using a microorganism of the genus *Flavobacterium* (Japanese Patent Application Publication No. 54-008749), a method of using a microorganism of the genus *Bacillus* (Japanese Patent Application Laid-Open No. 63-024895), a method of using a microorganism of the genus *Pseudomonas* (Japanese Patent Application Laid-Open No. 1-071476) and a method of using a microorganism of the genus *Arthrobacter* (J. Biotechnol. 46, 63, 1996) etc. In these L-amino acid-producing microorganisms, their N-carbamylamino acid hydrolase activity is often specific to L-amino acids. Accordingly, when DL-5-substituted hydantoin is used as the starting material, both D- and L-hydantoin is hydrolyzed to give N-carbamyl-DL-amino acids, out of which the N-carbamyl-L-amino acid is selectively hydrolyzed by the N-carbamylamino acid hydrolase, to finally give the L-amino acid only, as shown in the following reaction scheme (II).

L-Amino Acid-Producing Microorganism

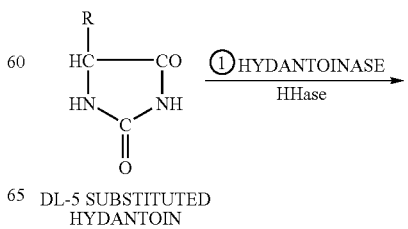

DL-5 SUBSTITUTED HYDANTOIN

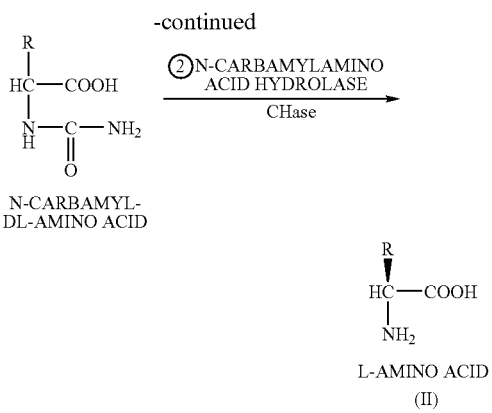

N-CARBAMYL-
DL-AMINO ACID

L-AMINO ACID (II)

From a microorganism of the genus *Flavobacterium* out of the L-amino acid-producing microorganisms mentioned above, hydantoinase and N-carbamylamino acid hydrolase are partially purified, and the hydantoinase is known to be able to act on both D- and L-configurations of 5-substituted hydantoin compounds (Agric. Biol. Chem., 51, 737 (1987)).

However, because the above enzyme preparation is obtained by partial purification, whether the action of the enzyme preparation is attributable to the single enzyme or not is unclear, and the amino acid sequence of the hydantoinase derived from *Flavobacterium* and the nucleotide sequence of its encoding gene are not revealed.

From a microorganism of the genus *Arthrobacter*, on one hand, a hydantoinase gene and N-carbamylamino acid hydrolase gene have been isolated, and it is known that L-amino acids can be produced by a recombinant prepared using the genes. However, the hydantoinase derived from a microorganism of the genus *Arthrobacter* does not act on DL-5-(4-hydroxybenzyl) hydantoin, and can thus not be used for production of L-tyrosine from DL-5-(4-hydroxybenzyl) hydantoin.

DISCLOSURE OF THE INVENTION

For efficient production of optically active amino acids, it is preferable to use a recombinant producing enzymes hydantoinase and N-carbamylamino acid hydrolase in higher amounts by isolating their genes, amplifying the genes and improving transcriptional and translational activity. However, there is no report on isolation of hydantoinase acting on DL-5-(4-hydroxybenzyl) hydantoin as a starting material for tyrosine, so there is a problem that hydantoinase widely available for synthesis of optically active amino acids represented by L-tyrosine cannot be produced efficiently by preparing a recombinant.

The cultured L-amino acid-producing microorganisms can be used to produce optically active amino acids from 5-substituted hydantoin compounds, but in this case, there are problems such as necessity for use of inducers such as hydantoin derivatives or use of a large amount of the cultured microorganisms in order to increase the amount of the enzymes.

Accordingly, the object of the present invention is to provide a method of efficiently producing optically active amino acids represented by L-tyrosine from 5-substituted hydantoin represented by 5-(4-hydroxybenzyl) hydantoin by isolating a hydantoinase gene and N-carbamylamino acid hydrolase gene from a microorganism having an ability to convert 5-(4-hydroxybenzyl) hydantoin into L-tyrosine to reveal the amino acid sequences of the enzymes and the nucleotide sequences of genes encoding therefor, and preparing a recombinant wherein the amount of the enzymes produced is increased to produce optically active amino acids efficiently.

As a result of extensive study in view of the problems described above, the present inventors successfully isolated a hydantoinase gene and N-carbamyl amino acid hydrolase gene from a microorganism having an ability to convert 5-(4-hydroxybenzyl) hydantoin into L-tyrosine, arriving at the present invention.

The present invention has following 32 characteristics:

(1) A DNA encoding for a protein having a hydantoinase activity, which has the following nucleotide sequence (a) or (b):

(a) the nucleotide sequence set forth in SEQ ID NO:1 in the Sequence Listing, and (b) a nucleotide sequence hybridizing under stringent conditions with DNA consisting of a nucleotide sequence complementary to the nucleotide sequence set forth in SEQ ID NO:1 in the Sequence Listing.

(2) A DNA encoding for a protein having a hydantoinase activity and having the following amino acid sequence (c) or (d):

(c) the amino acid sequence set forth in SEQ ID NO:2 in the Sequence Listing, and (d) an amino acid sequence wherein in the amino acid sequence set forth in SEQ ID NO:2 in the Sequence Listing, one or several amino acid residues are replaced, deleted, inserted, added or inverted.

(3) A recombinant DNA obtained by linking the DNA according to the item (1) or (2) to a vector DNA.

(4) The recombinant DNA according to the item (3), wherein the vector DNA is a pUC series plasmid, a pBR322 series plasmid, or a plasmid derived from derivatives thereof.

(5) A cell transformed with the recombinant DNA according to the item (3) or (4).

(6) The cell according to the item (5), wherein the cell is derived from *Escherichia coli*.

(7) A method of producing a protein having a hydantoinase activity, wherein the cell according to the item (5) or (6) is cultured in a medium, and a protein having a hydantoinase activity is accumulated in the medium and/or the cells.

(8) A protein having a hydantoinase activity, which has the following amino acid sequence (c) or (d):

(c) the amino acid sequence set forth in SEQ ID NO:2 in the Sequence Listing, and (d) the amino acid sequence wherein in the amino acid sequence set forth in SEQ ID NO:2 in the Sequence Listing, one or several amino acid residues are replaced, deleted, inserted, added or inverted.

(9) The protein according to the item (8), wherein the protein acts on at least DL-5-(4-hydroxybenzyl) hydantoin.

(10) A method of producing N-carbamylamino acids, comprising a process for producing a protein having a hydantoinase activity by the method according to the item (7) and a process for producing N-carbamylamino acids by allowing the protein having a hydantoinase activity to act on 5-substituted hydantoin.

(11) A method of producing optically active amino acids, comprising a process for producing a protein having a hydantoinase activity by the method according to the item (7) and a process for producing optically active amino acids by allowing the protein having a hydantoinase activity and an enzyme optico-selectively hydrolyzing N-carbamylamino acids or a material containing the enzyme to act on 5-substituted hydantoin.

(12) A method of producing optically active tyrosine, comprising a process for producing a protein having a hydantoinase activity by the method according to the item (7) and a process for producing optically active tyrosine by allowing the protein having a hydantoinase activity and an enzyme optico-selectively hydrolyzing N-carbamylamino acids or a material containing the enzyme to act on DL-5-(4-hydroxybenzyl) hydantoin.

(13) A DNA encoding for a protein having an N-carbamyl-L-amino acid hydrolase activity, which has the following nucleotide sequence (a) or (b):
(a) the nucleotide sequence set forth in SEQ ID NO:3 in the Sequence Listing, and
(b) the nucleotide sequence hybridizing under stringent conditions with DNA consisting of a nucleotide sequence complementary to the nucleotide sequence set forth in SEQ ID NO:3 in the Sequence Listing.

(14) A DNA encoding for a protein having an N-carbamyl-L-amino acid hydrolase activity and having the following amino acid sequence (c) or (d):
(c) the amino acid sequence set forth in SEQ ID NO:4 in the Sequence Listing, and
(d) the amino acid sequence wherein in the amino acid sequence set forth in SEQ ID NO:4 in the Sequence Listing, one or several amino acid residues are replaced, deleted, inserted, added or inverted.

(15) A recombinant DNA obtained by linking the DNA according to the item (13) or (14) to a vector DNA.

(16) The recombinant DNA according to the item (15), wherein the vector DNA is a pUC series plasmid, a pBR322 series plasmid, or a plasmid derived from derivatives thereof.

(17) A cell transformed with the recombinant DNA according to the item (15) or (16).

(18) A cell according to the item (17), wherein the cells are derived from *Escherichia coli*.

(19) A method of producing a protein having an N-carbamyl-L-amino acid hydrolase activity, wherein the cell according to the item (17) or (18) is cultured in a medium, and a protein having an N-carbamyl-L-amino acid hydrolase activity is accumulated in the medium and/or the cells.

(20) A protein having an N-carbamyl-L-amino acid hydrolase activity, which has the following amino acid sequence (c) or (d):
(c) the amino acid sequence set forth in SEQ ID NO:4 in the Sequence Listing, and
(d) the amino acid sequence wherein in the amino acid sequence set forth in SEQ ID NO:4 in the Sequence Listing, one or several amino acid residues are replaced, deleted, inserted, added or inverted.

(21) A method of producing L-amino acids, comprising a process for producing a protein having an N-carbamyl-L-amino acid hydrolase activity by the method according to the item (19) and a process for producing L-amino acids by allowing the protein having an N-carbamyl-L-amino acid hydrolase activity to act on N-carbamyl-L-amino acids.

(22) A method of producing L-amino acids, comprising a process for producing a protein having an N-carbamyl-L-amino acid hydrolase activity by the method according to the item (19) and a process for producing L-amino acids by allowing the protein having an N-carbamyl-L-amino acid hydrolase activity and an enzyme hydrolyzing 5-substituted hydantoin or a material containing the enzyme to act on 5-substituted hydantoin.

(23) A method of producing L-amino acids, comprising a process for producing a protein having a hydantoinase activity by the method according to the item (7), a process for producing a protein having an N-carbamyl-L-amino acid hydrolase activity by the method according to the item (19) and a process for producing L-amino acids by allowing the protein having a hydantoinase activity and the protein having an N-carbamyl-L-amino acid hydrolase activity to act on 5-substituted hydantoin.

(24) A method of producing L-tyrosine, comprising a process for producing a protein having a hydantoinase activity by the method according to the item (7), a process for producing a protein having an N-carbamyl-L-amino acid hydrolase activity by the method according to the item (19), and a process for producing L-tyrosine by allowing the protein having a hydantoinase activity and the protein having an N-carbamyl-L-amino acid hydrolase activity to act on DL-5-(4-hydroxybenzyl) hydantoin.

(25) A method of producing optically active N-carbamylamino acids, comprising recovering optically active amino acids produced by the method according to any of the items (11), (12) and (22) to (24).

(26) A method of producing optically active amino acids, comprising chemically or enzymatically converting optically active N-carbamylamino acids produced by the method according to the item (25) into amino acids.

(27) A structural gene group encoding for proteins involved in production of L-amino acids, which has the following nucleotide sequence (a) or (b):
(a) the nucleotide sequence set forth in SEQ ID NO:5 in the Sequence Listing, and
(b) the nucleotide sequence hybridizing under stringent conditions with DNA consisting of a nucleotide sequence complementary to the nucleotide sequence set forth in SEQ ID NO:5 in the Sequence Listing.

(28) A recombinant DNA obtained by linking the DNA according to the item (27) to a vector DNA.

(29) A cell transformed with the recombinant DNA according to the item (28).

(30) A method of producing a hybrid protein involved in production of L-amino acids, wherein a cell according to the item (29) is cultured in a medium, a hybrid protein involved in production of L-amino acids are accumulated in the medium and/or the cells, and the hybrid protein is recovered.

(31) A method of producing optically active amino acids, comprising a process for producing a hybrid protein involved in production of L-amino acids by the method according to the item (30) and a process of allowing the hybrid protein involved in production of L-amino acids to act on 5-substituted hydantoin.

(32) A method of producing optically active tyrosine, comprising a process for producing a hybrid protein involved in production of L-amino acids by the method according to the item (30) and a process of allowing the hybrid protein involved in production of L-amino acids to act on DL-5-(4-hydroxybenzyl) hydantoin.

BEST MODE FOR CARRYING OUT THE INVENTION

Figure 1:
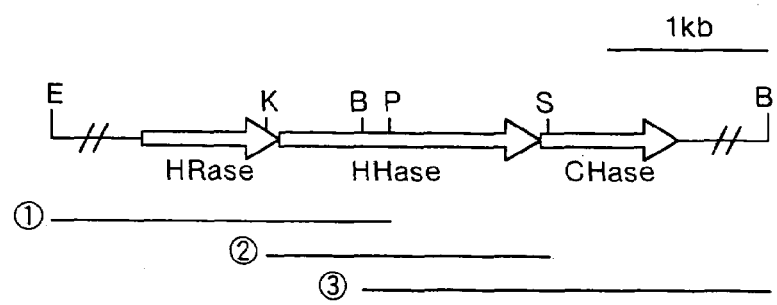
FIG. 1 is a diagram which shows the structure of a structural gene group encoding for hydantoin racemase, hydantoinase and N-carbamyl-L-amino acid hydrolase, respectively.

The embodiments of the present invention are explained in detail below while referring to the accompanying diagrams. An explanation about the invention will be given in the following order:

[I] DNA encoding for a protein having a hydantoinase activity and a protein having an N-carbamyl-L-amino acid hydrolase activity,

[II] Method of producing a protein having a hydantoinase activity and a protein having an N-carbamyl-L-amino acid hydrolase activity, and

[III] Method of producing an optically active amino acid.

In this specification, the protein having a hydantoinase activity is also referred to as hydantoinase, and the protein having an N-carbamylamino acid hydrolase activity is also referred to as N-carbamylamino acid hydrolase.

[I] DNA Encoding Hydantoinase and N-Carbamyl-L-Amino Acid Hydrolase

The DNA encoding hydantoinase and N-carbamyl-L-amino acid hydrolase according to the present invention was obtained in a process of study on hydantoin racemase and its DNA in *Aureobacterium liquefaciens* AJ3912 (FERM-P3133) described in Japanese Patent Application No. 2000-278571. *Flavobacterium* sp. AJ3912 (FERM-P3133) was initially deposited on Jun. 27, 1975 with the National Institute of Bioscience and Human-Technology, the Agency of Industrial Science of Technology, the Ministry of International Trade and Industry, Japan (at present, International Patent Organism Depositary (IPOD), National Institute of Advanced Industrial Science and Technology (AIST) (Chuo No. 6, Higashi 1-1-1, Tsukuba City, Ibaraki Pref., JP, 305-8566)), but it was revealed as a result of re-identification that this microorganism is classified into *Aureobacterium liquefaciens*. At present, the species of this microorganism is changed from *Aureobacterium liquefaciens* to *Microbacterium liquefaciens*, and the microorganism is deposited as *Microbacterium liquefaciens* AJ3912 (National Deposition No. FERM-P3133 and International Deposition No. FERM BP-7643, transferred on Jun. 27, 2001 under the International Deposition) with International Patent Organism Depositary (IPOD), National Institute of Advanced Industrial Science and Technology (AIST) (Chuo No. 6, Higashi 1-1-1, Tsukuba City, Ibaraki Pref., JP, 305-8566).

The physiological properties of *Microbacterium liquefaciens* AJ3912 (FERM-P3133) were examined in light of a microbial classification book, Berjey's [phonetic transcription] Manual of Determinative Bacteriology, Vol. 1 (9th edition, 1994, William & Wilkins Publishing Company), and the test results are shown in Table 1.

TABLE 1

Results of re-identification of *Microbacterium liquefaciens* AJ3912

| | |
|---|---|
| Gram stainability | positive |
| Form of cells | bacillus-shaped |
| Motility | none |
| Nitrate reduction | – |
| Pyrimidinase | – |
| Pyridonyl allyl amidase | – |
| Alkali phosphatase | + |
| β-Glucuronidase | – |
| β-Galactosidase | + |
| α-Glucosidase | + |
| N-Acetyl-β-glucosaminidase | + |
| Aesculin (glucosidase) | + |

TABLE 1-continued

Results of re-identification of *Microbacterium liquefaciens* AJ3912

| | |
|---|---|
| Urease | – |
| Gelatin liquefaction | + |
| Fermentability of hydrocarbons | |
| glucose | – |
| ribose | – |
| xylose | – |
| mannitol | – |
| maltose | – |
| lactose | – |
| Saccharose | – |
| glycogen | – |
| Anaerobic growth | – |
| Casein hydrolyzability | + |

The present inventors estimated that in isolation of a hydantoin racemase gene from *Aureobacterium liquefaciens* AJ3912 (FERM-P3133) as described in Japanese Patent Application No. 2000-278571, a simultaneously obtained nucleotide sequence downstream from the hydantoin racemase gene is a part of a hydantoinase gene, and this DNA fragment was amplified by the PCR method and utilized as the probe by which the full-length hydantoinase gene could be successfully isolated and obtained from a gene library of the bacterial strain. Similarly, the present inventors estimated that in isolation of the hydantoinase gene of the present invention, a nucleotide sequence downstream from the hydantoinase gene is a part of an N-carbamyl-L-amino acid hydrolase gene, and this DNA fragment was amplified by the PCR method and utilized as the probe by which the full-length N-carbamyl-L-amino acid hydrolase gene of the present invention could be successfully isolated and obtained.

That is, as shown in FIG. 1, the hydantoinase gene and the N-carbamyl-L-amino acid hydrolase gene of the present invention are considered to be downstream from the hydantoin racemase gene, to form an operon together with the hydantoin racemase gene. In FIG. 1, (1) is an EcoRI/PstI fragment, (2) is a KpnI/SacI fragment, and (3) is a fragment cleaved with BglII.

The operation in the PCR method used in isolation of the genes is described by White, T. J. et al., in Trends Genet. 5, 185 (1989), etc. The method of preparing chromosomal DNA and the method of isolating a desired DNA molecule from a gene library by use of a probe DNA molecule are described in Molecular Cloning, 2nd edition, Cold Spring Harbor Press (1989), etc.

The method of determining the nucleotide sequence of the isolated DNA encoding hydantoinase or N-carbamyl-L-amino acid hydrolase is described in A Practical Guide to Molecular Cloning, John Wiley & Sons, Inc. (1985), etc. Alternatively, the nucleotide sequence can be determined by use of a DNA sequencer manufactured by Applied Biosystems.

In the accompanying sequence listing of the present invention, the DNA encoding hydantoinase, specified by the method described above, is set forth in SEQ ID NO:1, and the DNA encoding N-carbamyl-L-amino acid hydrolase is set forth in SEQ ID NO:3. Further, the DNA encoding for a group of structural genes containing the hydantoin racemase gene, the hydantoinase gene and the N-carbamyl-L-amino acid hydrolase gene is set forth in SEQ ID NO:5.

These DNAs are those isolated from the chromosomal DNA in *Microbacterium liquefaciens* AJ3912 and encoding for the proteins involved in production of L-amino acids.

The amino acid sequence of a protein having a hydantoinase activity, encoded by the nucleotide sequence in SEQ ID NO:1 in the Sequence Listing, is set forth in SEQ ID NO:2 in the Sequence Listing, and the amino acid sequence of a protein having an N-carbamyl-L-amino acid hydrolase activity, encoded by the nucleotide sequence in SEQ ID NO:3 in the Sequence Listing, is set forth in SEQ ID NO:4 in the Sequence Listing. In addition, the amino acid sequence of a protein having a hydantoin racemase activity (hydantoin racemase shown in Japanese Patent Application No. 2000-278571), encoded by the hydantoin racemase gene contained in the structural gene group set forth in SEQ ID NO:5, is set forth in SEQ ID NO:6 in the Sequence Listing.

The protein having a hydantoinase activity set forth in SEQ ID NO:2 in the Sequence Listing and the protein having an N-carbamyl-L-amino acid hydrolase activity in SEQ ID NO:4 in the Sequence Listing catalyze the reaction of forming an optically active amino acid represented by L-tyrosine from 5-substituted hydantoin represented by 5-(4-hydroxybenzyl) hydantoin, as shown in the following reaction scheme (III):

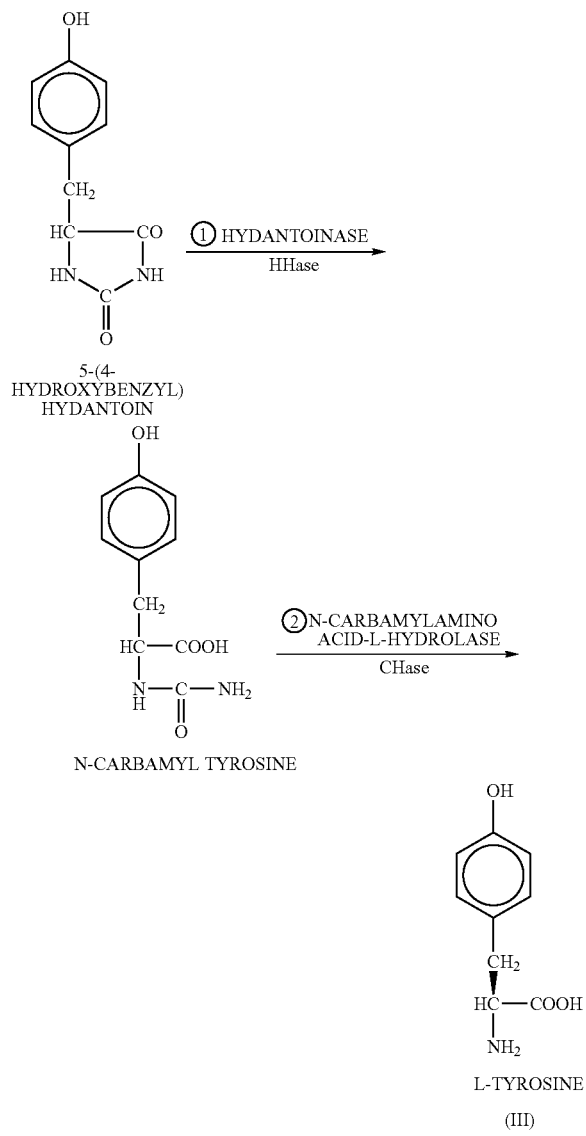

The DNA encoding hydantoinase and the DNA encoding N-carbamyl-L-amino acid hydrolase according to the present invention are described in more detail.

(1) DNA Encoding Hydantoinase

The hydantoinase gene of the present invention having the nucleotide sequence of SEQ ID NO:1 in the Sequence Listing was isolated from the chromosomal DNA in *Micobacterium liquefaciens* AJ3912 as described above, and has 79% homology (85% homology in amino acid sequence) with a known hydantoinase gene derived from a microorganism of the genus *Arthrobacter* (J. Biotechnol. 80, 217 (2000)), and has 44% homology (17% homology in amino acid sequence) with a known hydantoinase gene derived from a microorganism of the genus *Pseudomonas* (J. Biotechnol. 174, 962 (1992)).

The protein encoded by the DNA shown in SEQ ID NO:1 in the Sequence Listing is characterized by having a hydantoinase activity toward 5-(4-hydroxybenzyl) hydantoin. Accordingly, this protein can be utilized preferably in production of optically active amino acids represented by L-tyrosine.

The DNA encoding hydantoinase according to the present invention is not limited to the DNA shown in SEQ ID NO:1 in the Sequence Listing. That is, the DNA must have a difference in the nucleotide sequence thereof among species and strains belonging to the genera *Microbacterium* and *Flavobacterium*.

As a matter of course, the DNA of the present invention encompasses not only the isolated DNA encoding hydantoinase, but also any DNAs encoding for hydantoinase obtained by artificially mutating the isolated DNA encoding hydantoinase. As a method used frequently for artificial mutation, there is the site-specific mutagenesis method described in Method. in Enzymol., 154 (1987).

The DNA of the present invention also encompasses a DNA encoding for a protein having a hydantoinase activity and having a nucleotide sequence hybridizing under stringent conditions with a DNA consisting of a nucleotide sequence complementary to the nucleotide sequence set forth in SEQ ID NO:1 in the Sequence Listing. As used herein, the "stringent conditions" refer to those conditions under which a specific hybrid is formed whereas an unspecific hybrid is not formed. These conditions are hardly expressed explicitly numerically, but by way of example, mention is made of those conditions under which DNA molecules having higher homology e.g. preferably 80% or more, more preferably 90% or more homology, hybridize with each other while DNA molecules having lower homology do not hybridize with each other, or those conditions under which hybridization occurs under usual washing conditions in Southern hybridization, that is, at a salt concentration corresponding to 1×SSC and 0.1% SDS at 60° C., preferably 0.1×SSC and 0.1% SDS at 60° C. The "hydantoinase activity" refers to the activity of hydrolyzing 5-substituted hydantoin compounds to form N-carbamyl amino acids. However, the nucleotide sequence hybridizing under stringent conditions with DNA consisting of a nucleotide sequence complementary to the nucleotide sequence shown in SEQ ID NO:1 in the Sequence Listing has desirably about at least half of the enzyme activity of a protein having the amino acid sequence shown in SEQ ID NO:2 in the Sequence Listing.

The DNA of the present invention encompasses a DNA encoding for the substantially the same protein as hydantoinase encoded by the DNA shown in SEQ ID NO:1 in the Sequence Listing, that is, (a) DNA encoding for the amino acid sequence set forth in SEQ ID NO:2 in the Sequence Listing, and (b) DNA encoding for a protein having a hydantoinase activity, which has an amino acid sequence wherein in the amino acid sequence set forth in SEQ ID NO:2 in the Sequence Listing, one or several amino acid residues are replaced, deleted, inserted, added or inverted.

To deduce the encoding DNA on the basis of the amino acid sequence in (a) or (b) above, DNA universal codons of the nucleotide sequence may be adopted.

The term "several" means a number which results in no substantial deterioration of the steric structure or enzymatic activity of the amino acid residues, and which is typically 2 to 50, preferably 2 to 30, more preferably 2 to 10. Further, the "hydantoinase activity" means the activity of hydrolyzing 5-substituted hydantoinase compounds to form N-carbamylamino acids. However, the protein wherein in the amino acid sequence set forth in SEQ ID NO:2 in the Sequence Listing, one or several amino acid residues are replaced, deleted, inserted, added or inverted has desirably about at least half of the enzyme activity of a protein having the amino acid sequence set forth in SEQ ID NO:2 in the Sequence Listing.

(2) DNA Encoding N-carbamyl-L-amino Acid Hydrolase

The DNA encoding N-carbamyl-L-amino acid hydrolase according to the present invention is explained. The N-carbamyl-L-amino acid hydrolase gene of the present invention having the nucleotide sequence set forth in SEQ ID NO:3 in the Sequence Listing was isolated from the chromosomal DNA in *Microbacterium liquefaciens* AJ3912, and has 74.2% homology (81% homology in amino acid sequence) with a known N-carbamyl-L-amino acid hydrolase gene derived from a microorganism of the genus *Arthrobacter* (J. Biotechnol. 68, 101 (1999)). Further, this DNA has 47% homology (39% homology in amino acid sequence) with a known N-carbamyl-L-amino acid hydrolase gene derived from a microorganism of the genus *Pseudomonas* (J. Biotechnol. 174, 962 (1992)).

The DNA encoding N-carbamyl-L-amino acid hydrolase according to the present invention is not limited to the DNA shown in SEQ ID NO:3 in the Sequence Listing. That is, the DNA must have a difference in the nucleotide sequence thereof among species and strains belonging to the genera *Microbacterium* and *Flavobacterium*.

A DNA encoding N-carbamyl-L-amino acid hydrolase, even if obtained by artificially mutating the isolated DNA encoding N-carbamyl-L-amino acid hydrolase, is the DNA of the present invention. As a method used frequently for artificial mutation, there is the site-specific mutagenesis method described in Method. in Enzymol., 154 (1987).

The DNA of the present invention also encompasses a DNA encoding for a protein having an N-carbamyl-L-amino acid hydrolase activity and having a nucleotide sequence hybridizing under stringent conditions with a DNA consisting of a nucleotide sequence complementary to the nucleotide sequence set forth in SEQ ID NO:3 in the Sequence Listing. As used herein, the "stringent conditions" refer to those conditions under which a specific hybrid is formed whereas an unspecific hybrid is not formed. These conditions are hardly expressed explicitly numerically, but by way of example, mention is made of those conditions under which DNA molecules having higher homology e.g. preferably 80% or more, more preferably 90% or more homology, hybridize with each other while DNA molecules having lower homology do not hybridize with each other, or those conditions under which hybridization occurs under usual washing conditions in Southern hybridization, that is, at a salt concentration corresponding to 1×SSC and 0.1% SDS at 60° C., preferably 0.1×SSC and 0.1% SDS at 60° C. The "N-carbamyl-L-amino acid hydrolase activity" refers to the activity of hydrolyzing N-carbamylamino acids to form L-amino acids. However, the nucleotide sequence hybridizing under stringent conditions with DNA consisting of a nucleotide sequence complementary to the nucleotide sequence shown in SEQ ID NO:3 in the Sequence Listing has desirably about at least half of the enzyme activity of a protein having the amino acid sequence shown in SEQ ID NO:4 in the Sequence Listing.

The DNA of the present invention encompasses a DNA encoding for the substantially the same protein as N-carbamyl-L-amino acid hydrolase encoded by the DNA, that is, (a) DNA encoding for the amino acid sequence set forth in SEQ ID NO:4 in the Sequence Listing, and (b) DNA encoding for a protein having an N-carbamyl-L-amino acid hydrolase activity, which has an amino acid sequence wherein in the amino acid sequence set forth in SEQ ID NO:4 in the Sequence Listing, one or several amino acid residues are replaced, deleted, inserted, added or inverted.

To deduce the encoding DNA on the basis of the amino acid sequence in (a) or (b) above, DNA universal codons of the nucleotide sequence may be adopted.

The term "several" means a number which results in no substantial deterioration of the steric structure or enzymatic activity of the amino acid residues, and which is typically 2 to 50, preferably 2 to 30, more preferably 2 to 10. Further, the "N-carbamyl-L-amino acid hydrolase activity" means the activity of hydrolyzing N-carbamyl-L-amino acids to form L-amino acids. However, the protein wherein in the amino acid sequence set forth in SEQ ID NO:4 in the Sequence Listing, one or several amino acid residues are replaced, deleted, inserted, added or inverted has desirably about at least half of the enzyme activity of a protein having the amino acid sequence set forth in SEQ ID NO:4 in the Sequence Listing.

[II] Method of Producing Hydantoinase and N-carbamyl-L-amino Acid Hydrolase

The method of producing hydantoinase and N-carbamyl-L-amino acid hydrolase by recombinant DNA technology is explained. A large number of examples where useful proteins such as enzymes, physiologically active substances etc. are produced by utilizing recombinant DNA technology are known, and by use of recombinant DNA technology, useful proteins present in a very small amount in nature can be produced in a large amount.

Figure 2:
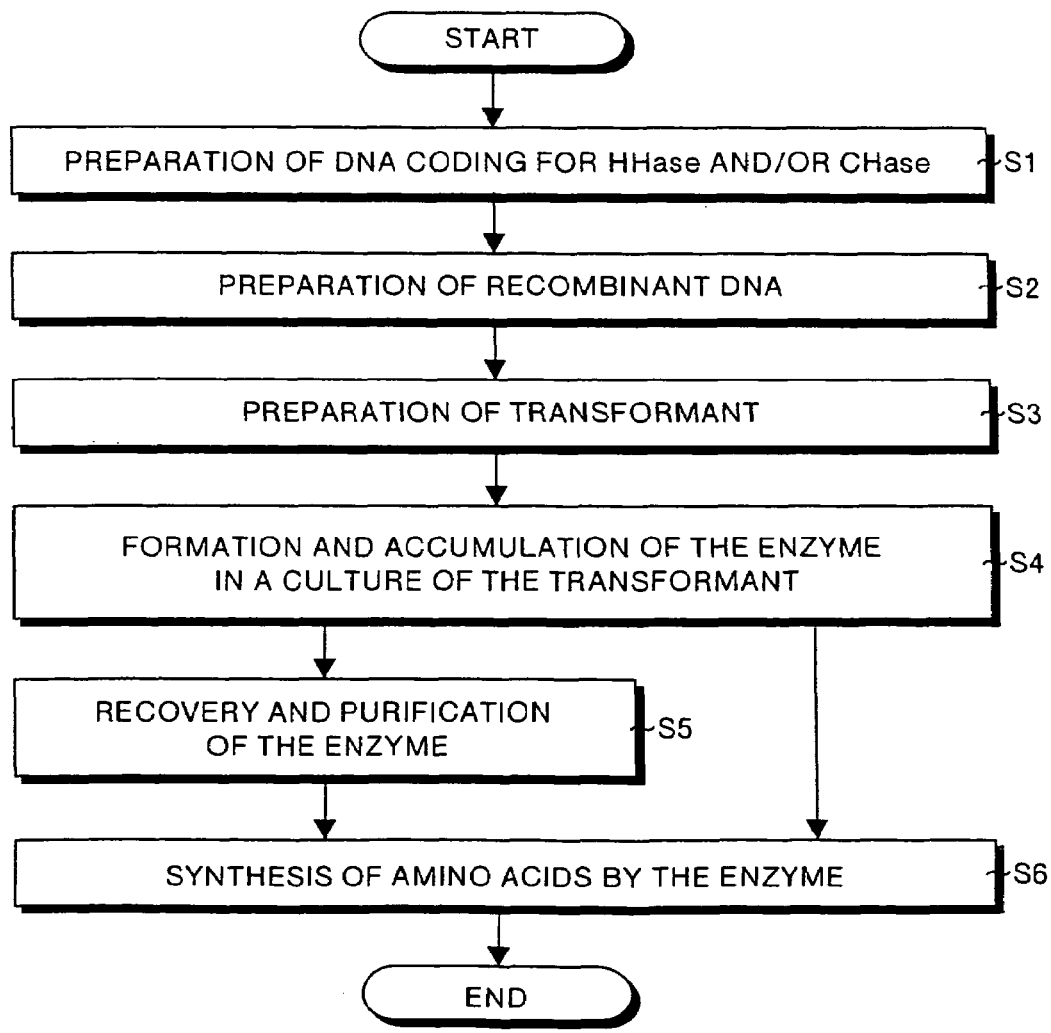
FIG. 2 is a flowchart which shows the process of producing hydantoinase and N-carbamyl-L-amino acid hydrolase according to the present invention.

FIG. 2 is a flowchart of the process of producing hydantoinase and N-carbamyl-L-amino acid hydrolase according to the present invention.

The hydantoinase gene of the present invention and/or the DNA encoding N-carbamyl-L-amino acid hydrolase is prepared (step S1).

The prepared DNA is ligated to a vector DNA to prepare a recombinant DNA (step S2), and cells are transformed with the recombinant DNA, to prepare a transformant (step. S3) Subsequently, the transformant is cultured in a medium to form and accumulate hydantoinase and/or N-carbamyl-L-amino acid hydrolase in the medium and/or cells (step S4).

Thereafter, the enzyme is recovered and purified in step S5, whereby the hydantoinase and/or N-carbamyl-L-amino acid hydrolase is produced in a large amount.

The enzyme produced in step S5 or the medium containing the enzyme accumulated therein in step S4 is used in synthesis of amino acid, whereby the desired optically active amino acid can be produced in a large amount (step S6).

The DNA ligated to the vector DNA may be any DNA capable of expressing the hydantoinase and/or N-carbamyl-L-amino acid hydrolase of the present invention.

As the hydantoinase gene ligated to the vector DNA, it is possible to use the above-described DNA, for example:

(a) DNA having the nucleotide sequence set forth in SEQ ID NO:1 in the Sequence Listing,
(b) DNA having a nucleotide sequence hybridizing under stringent conditions with DNA consisting of a nucleotide sequence complementary to the nucleotide sequence set forth in SEQ ID NO:1 in the Sequence Listing,
(c) DNA encoding for the amino acid sequence set forth in SEQ ID NO:2 in the Sequence Listing, and
(d) DNA encoding for an amino acid sequence wherein in the amino acid sequence set forth in SEQ ID NO:2 in the Sequence Listing, one or several amino acid residues are replaced, deleted, inserted, added or inverted.

As the N-carbamyl-L-amino acid hydrolase gene ligated to the vector DNA, it is possible to use e.g. the following DNAs:

(a) DNA having the nucleotide sequence set forth in SEQ ID NO: 3 in the Sequence Listing,
(b) DNA having a nucleotide sequence hybridizing under stringent conditions with DNA consisting of a nucleotide sequence complementary to the nucleotide sequence set forth in SEQ ID NO:3 in the Sequence Listing,
(c) DNA encoding for the amino acid sequence set forth in SEQ ID NO:4 in the Sequence Listing, and
(d) DNA encoding for an amino acid sequence wherein in the amino acid sequence set forth in SEQ ID NO:4 in the Sequence Listing, one or several amino acid residues are replaced, deleted, inserted, added or inverted.

In addition to these DNAs, use can be made of DNA comprising the hydantoinase gene ligated to the N-carbamyl-L-amino acid hydrolase gene or DNA having the nucleotide sequence shown in SEQ ID NO:5 in the Sequence Listing. In the case of the former, the hydantoinase of the present invention and the N-carbamyl-L-amino acid hydrolase of the present invention will be simultaneously expressed, while in the case of the latter, not only the hydantoinase and N-carbamyl-L-amino acid hydrolase of the present invention but also hydantoin racemase will be expressed.

When the protein is to be produced in a large mount by recombinant DNA technology, host cells to be transformed can make use of microbial cells, *Actinomyces* cells, yeast cells, fungal cells, plant cells, animal cells etc. Because there are generally a large number of findings on production of proteins in a large amount by use of colon bacteria, it is preferable to use *Escherichia coli*. Hereinafter, the method of producing hydantoinase and/or N-carbamyl-L-amino acid hydrolase by use of transformed colon bacteria is explained.

As the promoter expressing the DNA encoding hydantoinase and/or N-carbamyl-L-amino acid hydrolase, a promoter ordinarily used in production of a protein in colon bacteria can be used, and mention can be made of strong promoters such as, for example, T7 promoter, trp promoter, lac promoter, tac promoter, PL promoter etc.

To increase the amount of the protein produced, a terminator that is a transcription termination sequence is preferably ligated to a downstream region of the protein gene. The terminator includes T7 terminator, fd phage terminator, T4 terminator, a terminator for tetracycline resistance gene, a terminator for colon bacteria trp A gene, etc.

The vector for introducing the gene encoding for hydantoinase and/or N-carbamyl-L-amino acid hydrolase into host cells is preferably the so-called multicopy vector, and includes plasmids having an origin of replication derived from Col E1, for example, pUC series plasmids, pBR322 series plasmids or derivatives thereof. The "derivatives" are those obtained by modifying plasmids by replacement, deletion, insertion, addition or inversion of some nucleotides. The modification referred to here includes modification by natural mutation or by mutation treatment with a mutagen or UV irradiation.

To select the transformant, the vector preferably has a marker such as ampicillin resistance gene etc., and as such plasmids, expression vectors having a strong promoter are commercially available; for example, pUC series (manufactured by Takara Shuzo Co., Ltd.), PPROK series (manufactured by Clontech), pKK233-2 (manufactured by Clontech) etc.

The DNA fragment having a promoter, the gene encoding for hydantoinase and/or N-carbamyl-L-amino acid hydrolase, and a terminator ligated in this order can be ligated to the vector DNA to give a recombinant DNA.

The recombinant DNA is used to transform host cell, and by culturing the cells, the hydantoinase and/or N-carbamyl-L-amino acid hydrolase is expressed and produced. As the method of transformation and the method of selecting the transformant, those described in Molecular Cloning, 2nd edition, Cold Spring Harbor Press (1989), etc. can be used.

The production medium used may be a medium such as M9-casamino acid medium, LB medium etc. which are usually used for culturing colon bacteria. Further, the culture conditions and production-inducing conditions are selected suitably depending on the marker and promoter in the vector used, the type of the host microorganism, etc. To increase the amount of the enzyme produced, addition of isopropyl-1-thio-β-D-galactopyranoside (IPTG) to the medium or enzyme-inducing treatments such as an increase in temperature are also preferable.

After the cultured microorganism is collected by centrifugation etc., the microorganism is disrupted or lyzed, and hydantoinase and/or N-carbamyl-L-amino acid hydrolase can be recovered and used as a crude enzyme. Disruption of the microorganism can make use of methods such as disruption by sonication, disruption by a French press, disruption by glass beads etc.; or when the microorganism is to be lyzed, a method of treatment with egg white lysozyme or a peptidase or a method of suitable combination thereof is used. As necessary, these enzymes can be used in a pure form after purification by conventional techniques such as precipitation, filtration and column chromatography. In this case, a method of purification with an antibody against these enzymes can also be used.

The hydantoinase of the present invention obtained by the method of using the recombinant described above is a protein having a hydantoinase activity, which has the following amino acid sequence (a) or (b):

(a) the amino acid sequence set forth in SEQ ID NO:2 in the Sequence Listing, and
(b) an amino acid sequence wherein in the amino acid sequence set forth in SEQ ID NO:2 in the Sequence Listing, one or several amino acid residues are replaced, deleted, inserted, added or inverted.

The N-carbamyl-L-amino acid hydrolase of the present invention obtained by the method of using the recombinant described above is a protein having an N-carbamyl-L-amino acid hydrolase activity, which has the following amino acid sequence (a) or (b):

(a) the amino acid sequence set forth in SEQ ID NO:4 in the Sequence Listing, and (b) an amino acid sequence wherein in the amino acid sequence set forth in SEQ ID NO:4 in the Sequence Listing, one or several amino acid residues are replaced, deleted, inserted, added or inverted.

The "one or several amino acid residues", "hydantoinase activity" and "N-carbamyl-L-amino acid hydrolase activity" have the same meanings as defined in the item [I] DNA encoding hydantoinase and N-carbamyl-L-amino acid hydrolase.

[III] Method of Producing an Optically Active Amino Acid

The method of producing an optically active amino acid by use of the hydantoinase and/or N-carbamyl-L-amino acid hydrolase according to the present invention is explained.

The method of producing an optically active amino acid according to the present invention comprises use of the enzyme of the present invention as hydantoinase and/or N-carbamyl-L-amino acid hydrolase, and there can be the following 3 combinations of hydantoinase and N-carbamyl-L-amino acid hydrolase:

(i) hydantoinase of the present invention+N-carbamylamino acid hydrolase, (ii) hydantoinase+N-carbamyl-L-amino acid hydrolase of the present invention, and (iii) hydantoinase of the present invention+N-carbamyl-L-amino acid hydrolase of the present invention.

In case (i), the hydantoinase of the present invention includes a protein having a hydantoinase activity, which has the following amino acid sequence (a) or (b):

(a) the amino acid sequence set forth in SEQ ID NO:2 in the Sequence Listing, and (b) an amino acid sequence wherein in the amino acid sequence set forth in SEQ ID NO:2 in the Sequence Listing, one or several amino acid residues are replaced, deleted, inserted, added or inverted.

The hydantoinase obtained by culturing cells transformed with a recombinant DNA obtained by ligating the DNA encoding for such hydantoinase to a vector can also be used. When the hydantoinase is produced by the transformed cells, a substrate may be added directly to a culture liquid thereof during culturing, and either the microorganism separated from the culture liquid or the washed microorganism can be used. Further, a treated microbial material prepared by disrupting or lyzing the microorganism may be used as it is, or the hydantoinase may be recovered from the treated microbial material and used as a crude enzyme solution, and the enzyme may be further purified before use. That is, the enzyme and materials containing the enzyme as fractions having a hydantoinase activity can be used. The "materials containing the enzyme" may be any materials containing the enzyme, and include e.g. a culture, a cultured microorganism, a washed microorganism, a treated microbial material obtained by disrupting or lyzing the microorganism, a crude enzyme solution, a purified enzyme, etc.

As the substrate for the hydantoinase of the present invention, any 5-substituted hydantoin compounds which can be hydrolyzed with the substrate specificity of the enzyme, and both D- and L-5-substituted hydantoin compounds can be used. For example, mention is made of 5-substituted hydantoin compounds corresponding to naturally occurring amino acids, typically DL-5-benzyl hydantoin, DL-5-(4-hydroxybenzyl) hydantoin, DL-5-indolyl methyl hydantoin, DL-5-(3,4-dihydroxybenzyl) hydantoin, DL-5-methyl thioethyl hydantoin, DL-5-isobutyl hydantoin, DL-5-carbamyl ethyl hydantoin and DL-5-carbamyl methyl hydantoin, etc. and 5-substituted hydantoin compounds corresponding to non-naturally occurring amino acids, typically DL-5-benzyl oxymethyl hydantoin, DL-5-(3,4-methylene dioxybenzyl) hydantoin, DL-5-(3,4-dimethoxybenzyl) hydantoin, DL-5-methoxymethyl hydantoin, and DL-5-(4-methyl-4-nitropentyl) hydantoin, etc. as well as 5-substituted hydantoin compounds corresponding to derivatives of the above.

As the N-carbamylamino acid hydrolase used in combination with the hydantoinase of the present invention, the known enzyme catalyzing the reaction of forming an amino acid by acting on N-carbamylamino acid to hydrolyze the substance, or materials containing the enzyme, can be used without particular limitation. The "materials containing the enzyme" may be any materials containing the enzyme, and include e.g. a culture, a cultured microorganism, a treated microbial material obtained by disrupting or lyzing the microorganism, a crude enzyme solution, a purified enzyme, etc. However, the hydantoinase of the present invention does not have optical selectivity, so when optically active amino acids are to be produced from DL-5-substituted hydantoin compounds as the starting material, optically selective N-carbamylamino acid hydrolase should be used. The presence of N-carbamyl-D-amino acid hydrolase selectively hydrolyzing a D-configuration of N-carbamylamino acid in for example *Pseudomonas* sp. AJ11220 (Japanese Patent Application Publication No. 56-003034) is known. As a result of re-identification, *Pseudomonas* sp. AJ11220 is revealed to belong *Agrobacterium* sp. *Agrobacterium* sp. AJ11220 is a microorganism deposited on Dec. 20, 1977 as FERM-P4347 with the National Institute of Bioscience and Human-Technology, the Agency of Industrial Science of Technology, the Ministry of International Trade and Industry, JP and transferred on Jun. 27, 2001 as FERM BP-7645 under the Budapest Treaty to International Patent Organism Depositary (IPOD), National Institute of Advanced Industrial Science and Technology (AIST) (Chuo No. 6, Higashi 1-1-1, Tsukuba City, Ibaraki Pref., JP, 305-8566). Further, the presence of N-carbamyl-L-amino acid hydrolase selectively hydrolyzing the L-configuration of N-carbamylamino acid in e.g. *Bacillus* sp. AJ12299 (Japanese Patent Application Laid-Open No. 63-024894) besides *Microbacterium liquefaciens* AJ3912 shown in the present invention is known. *Bacillus* sp. AJ12299 is a microorganism deposited on Jul. 5, 1986 under FERM-P8837 with the National Institute of Bioscience and Human-Technology, the Agency of Industrial Science of Technology, the Ministry of International Trade and Industry, JP and transferred on Jun. 27, 2001 as FERM BP-7646 under the Budapest Treaty to International Patent Organism Depositary (IPOD), National Institute of Advanced Industrial Science and Technology (AIST) (Chuo No. 6, Higashi 1-1-1, Tsukuba City, Ibaraki Pref., JP, 305-8566).

The case (ii) will now be explained. The N-carbamyl-L-amino acid hydrolase of the present invention includes a protein having an N-carbamyl-L-amino acid hydrolase activity, which has the following amino acid sequence (a) or (b):

(a) the amino acid sequence set forth in SEQ ID NO:4 in the Sequence Listing, and (b) an amino acid sequence wherein in the amino acid sequence set forth in SEQ ID NO:4 in the Sequence Listing, one or several amino acid residues are replaced, deleted, inserted, added or inverted.

The N-carbamyl-L-amino acid hydrolase obtained by culturing cells transformed with a recombinant DNA obtained by ligating the DNA encoding for such N-carbamyl-L-amino acid hydrolase to a vector can also be used. When the N-carbamyl-L-amino acid hydrolase is produced by the transformed cells, a substrate may be added directly to a culture liquid thereof during culturing, and either the microorganism separated from the culture or the washed microorganism can be used. Further, a treated microbial material prepared by disrupting or lyzing the microorganism may be used as it is, or the N-carbamyl-L-amino acid hydrolase may be recovered from the treated microbial material and used as a crude enzyme solution, and the enzyme may be further purified before use. That is, the enzyme and materials containing the enzyme as fractions having an N-carbamyl-L-amino acid hydrolase activity can be used. The "materials containing the enzyme" may be any materials containing the enzyme, and include e.g. a culture, a cultured microorganism, a washed microorganism, a treated microbial material obtained by disrupting or lyzing the microorganism, a crude enzyme solution, a purified enzyme, etc.

As the substrate for the N-carbamyl-L-amino acid hydrolase of the present invention, any N-carbamyl-L-amino acids which can be hydrolyzed with the substrate specificity of the enzyme can be used. That is, not only N-carbamyl-L-amino acids obtained from the 5-substituted hydantoin compounds described above, but also N-carbamyl-L-serine, N-carbamyl-L-glycine, N-carbamyl-L-isoleucine, N-carbamyl-L-valine, N-carbamyl-L-alanine and N-carbamyl-β-alanine, etc. can be used as the substrate.

As the hydantoinase used in combination with the N-carbamyl-L-amino acid hydrolase of the present invention, the known enzyme catalyzing the reaction of forming N-carbamylamino acid by acting on a 5-substituted hydantoin compound to hydrolyze the substance, or materials containing the enzyme, can be used without particular limitation. The "materials containing the enzyme" may be any materials containing the enzyme, and include e.g. a culture, a cultured microorganism, a treated microbial material obtained by disrupting or lyzing the microorganism, a crude enzyme solution, a purified enzyme, etc. However, the N-carbamyl-L-amino acid hydrolase of the present invention is specific to L-configuration, so optical specificity-free hydantoinase or hydantoinase acting specifically on L-configuration should be used. The presence of the optical specificity-free hydantoinase in e.g. *Arthrobacter aurescens* besides *Microbacterium liquefaciens* AJ3912 shown in the present invention is known (J. Biotechnol. 61, 1 (1998)). Further, the presence of the hydantoinase acting specifically on the L configuration of hydantoin compound in e.g. *Bacillus* sp. AJ12299 (Japanese Patent Application Laid-Open No. 63-024894) is known. *Bacillus* sp. AJ12299 is a microorganism deposited on Jul. 5, 1986 under FERM-P8837 with the National Institute of Bioscience and Human-Technology, the Agency of Industrial Science of Technology, the Ministry of International Trade and Industry, JP and transferred on Jun. 27, 2001 as FERM BP-7646 under the Budapest Treaty to International Patent Organism Depositary (IPOD), National Institute of Advanced Industrial Science and Technology (AIST) (Chuo No. 6, Higashi 1-1-1, Tsukuba City, Ibaraki Pref., JP, 305-8566).

The case (iii) will now be explained. In case (iii), the hydantoinase of the present invention described in (i) is used in combination with the N-carbamyl-L-amino acid hydrolase of the present invention explained in (ii). Among the combinations in (i) to (iii), the most preferable combination is (iii).

In the reaction process, a mixture of the hydantoinase and N-carbamyl-L-amino acid hydrolase may be allowed to react on 5-substituted hydantoin compounds, or the hydantoinase and N-carbamyl-L-amino acid hydrolase may be successively allowed to react on 5-substituted hydantoin compounds. From the viewpoint of simplification of the reaction process, the former method is preferable.

When the hydrolysis activity of the hydantoinase is free of optical selectivity and the N-carbamylamino acid hydrolase has optical activity when DL 5-substituted hydantoin compounds are converted into optically active amino acids, the formed amino acids will be either D- or L-optically active amino acids while the unreacted enantiomer N-carbamylamino acids will remain in the reaction solution. That is, when L-amino acids are formed by selectively decomposing N-carbamyl-L-amino acids by the N-carbamylamino acid hydrolase, N-carbamyl-D-amino acids will remain; on the other hand, when D-amino acids are formed, N-carbamyl-L-amino acids will remain.

Even in this case, however, the hydantoinase slightly catalyze the reverse reaction i.e. dehydration and condensation of the remaining unreacted enantiomer N-carbamylamino acids, to form 5-substituted hydantoin compounds again.

Accordingly, the optically active amino acids can be produced in a molar ratio of 50% or more from DL 5-substituted hydantoin compounds by combination with spontaneous racemization or chemical racemization of 5-substituted hydantoin compounds or racemization reaction by hydantoin racemase.

In other words, it is preferable to further use hydantoin racemase in addition to the hydantoinase and N-carbamyl-L-amino acid hydrolase. As the hydantoin racemase, hydantoin racemase derived from *Aureobacterium liquefaciens* AJ3912 (FERM-P 3133) described in Japanese Patent Application No. 2000-278571 can be preferably used. In this case, a hybrid protein consisting of hydantoin racemase, hydantoinase and N-carbamyl-L-amino acid hydrolase obtained by culturing cells transformed with a recombinant DNA obtained by ligating, to a vector, a structural gene group shown in SEQ ID NO:5 encoding for the proteins involved in production of L-amino acid can also be used. When the hybrid protein is used, the hydantoin racemase contained in the hybrid protein catalyzes racemization of 5-substituted hydantoin compounds, and thus L-amino acids can be obtained theoretically 100% yield from DL 5-substituted hydantoin compounds as shown in the following reaction scheme (IV). When the hybrid protein is used, the hydantoinase also catalyzes a reverse reaction of a reaction that produces an N-carbamylamino acid by splitting or causing cleavage of a hydantoin ring. In other words, the hydantoinase catalyzes the reverse reaction that produces 5-substituted hydantoin from N-carbamylamino acid. Therefore, L-amino acid may be produced also from N-carbamyl-D-amino acid.

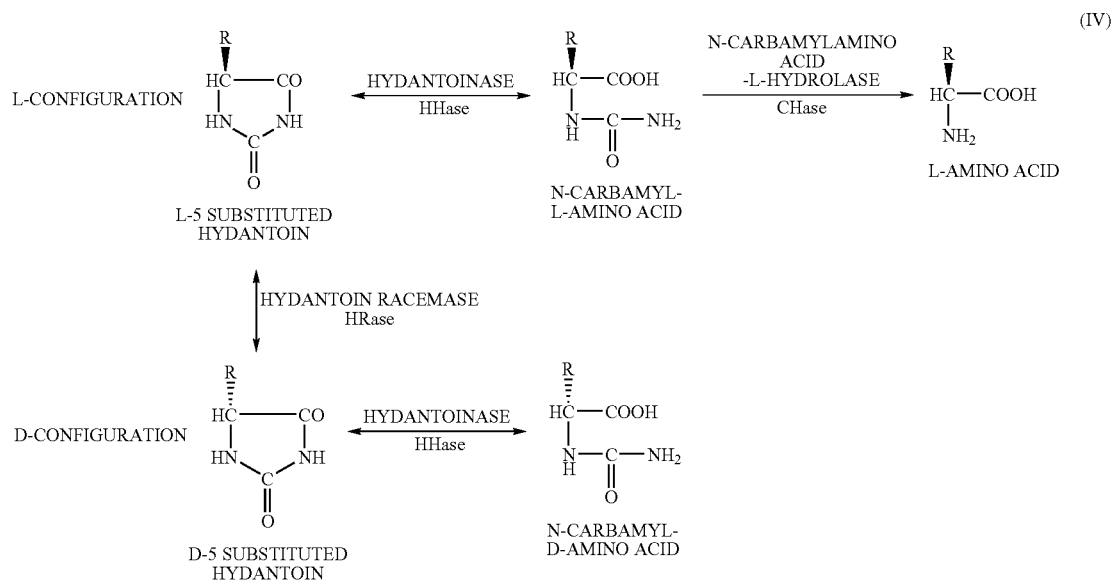

(IV)

The hybrid protein can also be used to produce N-carbamylamino acids. For example, N-carbamylamino acids can be produced by adding e.g. an inhibitor of the N-carbamyl-L-amino acid hydrolase to the hybrid protein, to terminate the hydrolysis reaction at the stage of N-carbamylamino acids.

In production of optically active amino acids, the remaining N-carbamylamino acids may be separated and recovered from optically active amino acid, whereby the N-carbamylamino acids can be produced. Further, amino acids can then be produced by allowing the N-carbamylamino acid hydrolase or materials containing the enzyme to act on the N-carbamylamino acids; or by chemical hydrolysis treatment with nitrite etc., the amino acids can also be produced in higher yield maintaining optical activity.

The presence of N-carbamyl-D-amino acid hydrolase selectively hydrolyzing the D-configuration of N-carbamylamino acid in e.g. *Pseudomonas* sp. AJ11220 is known (Japanese Patent Application Publication No. 56-003034). As a result of re-identification, *Pseudomonas* sp. AJ11220 is revealed to belong *Agrobacterium* sp. *Agrobacterium* sp. AJ11220 is a microorganism deposited on Dec. 20, 1977 as FERM-P4347 with the National Institute of Bioscience and Human-Technology, the Agency of Industrial Science of Technology, the Ministry of International Trade and Industry, JP and transferred on Jun. 27, 2001 as FERM BP-7645 under the Budapest Treaty to International Patent Organism Depositary (IPOD), National Institute of Advanced Industrial Science and Technology (AIST) (Chuo No. 6, Higashi 1-1-1, Tsukuba City, Ibaraki Pref., JP, 305-8566). Further, the presence of N-carbamyl-L-amino acid hydrolase selectively hydrolyzing the L-configuration of N-carbamylamino acid in e.g. *Bacillus* sp. AJ12299 (Japanese Patent Application Laid-Open No. 63-024894) besides *Microbacterium liquefaciens* AJ3912 shown in the present invention is known. *Bacillus* sp. AJ12299 is a microorganism deposited on Jul. 5, 1986 under FERM-P8837 with the National Institute of Bioscience and Human-Technology, the Agency of Industrial Science of Technology, the Ministry of International Trade and Industry, JP and transferred on Jun. 27, 2001 as FERM BP-7646 under the Budapest Treaty to International Patent Organism Depositary (IPOD), National Institute of Advanced Industrial Science and Technology (AIST) (Chuo No. 6, Higashi 1-1-1, Tsukuba City, Ibaraki Pref., JP, 305-8566).

When a culture liquid of cells transformed with the recombinant DNA obtained by linking the DNA encoding hydantoinase and/or N-carbamyl-L-amino acid hydrolase to a vector DNA, or a separated microorganism, a washed microorganism, a treated microbial material, or a crude enzyme solution or a purified enzyme obtained from the treated microbial material is used for progress of the amino acid-forming reaction, a reaction solution containing 5-substituted hydantoin compounds or N-carbamylamino acid, and the culture liquid, the separated microorganism, the washed microorganism, the treated microbial material, the crude enzyme solution, or the purified enzyme is adjusted to a suitable temperature of 25 to 40° C. and left or stirred for 8 hours to 5 days while the pH is kept at 5 to 9.

When the cells transformed with the recombinant DNA obtained by linking the DNA encoding hydantoinase and/or N-carbamyl-L-amino acid hydrolase to a vector DNA are cultured in a water-soluble medium to proceed the amino acid-forming reaction, use is made of a water-soluble medium containing 5-substituted hydantoin compounds or N-carbamylamino acid, nutrients such as a carbon source, a nitrogen source, and inorganic ions necessary for growth of the transformed cells. Further, desirable results are often obtained by adding a very small amount of organic nutrients such as vitamins, amino acids etc. The 5-substituted hydantoin compounds may be added in divided portions. Culturing is conducted preferably for 8 hours to 5 days under aerobic conditions while maintaining a suitable range of pH 5 to 9 and a temperature of 25 to 40° C.

The formed amino acids can be separated and purified by techniques known in the art. For example, there is a method of adsorbing basic amino acids by contacting with an ion-exchange resin and then eluting them, followed by crystallization thereof or discoloration and filtration thereof through activated carbon and subsequent crystallization.

EXAMPLES

Hereinafter, the present invention is explained in more detail by reference to Examples 1 to 5. The present invention is not limited to the description of the Examples.

Example 1

Isolation of a Hydantoinase Gene and an N-carbamyl-L-amino Acid Hydrolase Gene

As described above, the present inventors estimated that in isolation and purification of a hydantoin racemase gene from cultured *Microbacterium liquefaciens* AJ3912, a simultaneously obtained nucleotide sequence downstream from the hydantoin racemase gene is a part of a hydantoinase gene because of homology thereof with a known hydantoinase gene, and further estimated that an N-carbamyl-L-amino acid hydrolase gene can be present downstream therefrom, and thus the inventors utilized such DNA fragment as the probe by which the full-length hydantoinase gene and the full-length N-carbamyl-L-amino acid hydrolase gene were obtained from a gene library of the above strain. For configuration of the gene library, *E. coli* JM109 was used as the host, and pUC18 or pUC19 was used as the vector.

1. Acquisition of the Microorganism

*Microbacterium liquefaciens* AJ3912 was refreshed by culturing it at 30° C. for 24 hours in CM2G agar medium (0.5 g/dl glucose, 1.0 g/dl yeast extract, 1.0 g/dl peptone, 0.5 g/dl NaCl, 2 g/dl agar, pH 7.0). The microorganism was inoculated via one loop of platinum into a 500-ml Sakaguchi flask containing 50 ml CM2G liquid medium, and then cultured under shaking at 30° C. for 16 hours under aerobic conditions.

2. Acquisition of the Chromosomal DNA from the Microorganism 50 ml of the culture liquid was centrifuged (12,000×g, 4° C., 15 minutes), whereby the microorganism was collected. This microorganism was suspended in 10 ml of 50:20 TE (50 mM Tris-HCl (pH 8.0), 20 mM EDTA), washed and centrifuged, whereby the microorganism was recovered, and then this microorganism was suspended again in 10 ml of 50:20 TE. 0.5 ml of 20 mg/ml lysozyme solution and 1 ml of 10% SDS solution were added to the above suspension, followed by incubation at 55° C. for 20 minutes. After incubation, a 1-fold volume of 10:1 TE-saturated phenol was added thereto to remove proteins. A 1-fold volume of 2-propanol was added to the separated aqueous layer, to precipitate and recover DNA. After the precipitated DNA was dissolved in 0.5 ml of 50:20 TE, 5 µl of 10 mg/ml RNase and 5 µl of 10 mg/ml Proteinase K were added thereto and the mixture was reacted at 55° C. for 2 hours. After reaction, a 1-fold volume of 10:1 TE-saturated phenol was added thereto to remove proteins. Further, a 1-fold volume of 24:1 chloroform/isoamyl alcohol was added to the separated aqueous layer and stirred, and the aqueous layer was recovered. This procedure was repeated further twice, and 3 M sodium acetate solution (pH 5.2) was added at a final concentration of 0.4 M to the resulting aqueous layer, followed by adding a 2-fold volume of ethanol thereto. The DNA occurring as precipitates was recovered, washed with 70% ethanol, dried and dissolved in 1 ml of 10:1 TE.

3. Isolation of the Hydantoinase Gene

By a method described in Japanese Patent Application No. 2001-278739, it was confirmed that in an about 2.9 kb EcoRI/PstI fragment ((1) in FIG. 1) obtained from the chromosomal DNA in *Microbacterium liquefaciens* AJ3912, there is an open reading frame (ORF) encoding for a protein containing an N-terminal amino acid sequence of hydantoin racemase, and that this gene is a gene encoding for hydantoin racemase having 48% homology with a known hydantoin racemase derived from a microorganism of the genus *Pseudomonas* (J. Bacteriol., 174, 962 (1992)). In this 2.9 kb fragment, a downstream region of about 600 nucleotides from the hydantoin racemase gene was examined for homology, and as a result, it was confirmed that a region of from the nucleotide at the 18-position (from the termination codon of the hydantoin racemase gene) to PstI site has homology with a known hydantoinase. Accordingly, a part of this sequence was used in an attempt at acquisition of the full-length hydantoinase gene. The contents of the patent applications supra are incorporated by reference into this specification.

4. Isolation of the Hydantoinase Gene from the Gene Library

Southern hybridization was carried out for acquisition of the full-length hydantoinase gene. By PCR where the chromosomal DNA from *Microbacterium liquefaciens* AJ3912 was used as the template while the oligonucleotides shown in Table 2 were used as primers, a fragment (about 500 bp in the above region of about 600 bp) was amplified and used as the probe. The amplified fragment was prepared at a concentration of about 50 nm/µl, and as the probe, 16 µl of this DNA solution was labeled with DIG by incubation at 37° C. for 24 hours according to a protocol of DIG High Prime (Boehringer Mannheim).

Table 2

Primers used for preparation of the probe for acquisition of the hydantoinase gene

| Primer No. | Sequence | |
|---|---|---|
| 10 | CTGCAGCGTCTGGATGAGCATCTCGTTCT CGG | SEQ ID NO:7 |
| 16 | ATCGATGCCGCAGGCAGGTTCGTGATGCC | SEQ ID NO:8 |

1 µg chromosomal DNA was completely digested with a combination of various restriction enzymes, subjected to electrophoresis on 0.8% agarose gel, and blotted onto a nylon membrane (Boehringer Mannheim, Nylon membranes positively charged). Subsequently, Southern hybridization was conducted according to the conventional method. Hybridization was carried out using DIG Easy Hyb (Boehringer Mannheim), and after pre-hybridization at 50° C. for 30 minutes, the probe was added and hybridized at 50° C. for 18 hours. The sample was detected using a DIG Nucleotide Detection Kit (Boehringer Manheim).

As a result, a band was detected at a position of about 1.5 kb in a KpnI/SacI-cleaved product ((2) in FIG. 1). Accordingly, a fragment of about 1.5 kb was recovered from the cleaved product and ligated to pUC19, to prepare a library (450 strains) of *E. coli* JM109, followed by colony hybridization. The colonies were transferred onto a nylon membrane filter (Boehringer Mannheim, Nylon membranes for colony and plaque hybridization) and subjected to treatments such as alkali denaturation, neutralization and immobilization. Hybridization was conducted using DIG Easy Hyb, pre-hybridization was conducted at 42° C. for 30 minutes, and then the DIG-labeled probe described above was added thereto and hybridized at 42° C. for 18 hours. Five positive clones were selected by detecting with a DIG Nucleotide Detection Kit.

The plasmid carried on the selected clones was prepared according to a method described in Molecular Cloning, 2nd edition, Cold Spring Harbor Press (1989), and the nucleotide sequence of the inserted fragment was determined. As a result, an about 1.4-kb open reading frame (ORF) was present downstream from the hydantoin racemase gene, and estimated to be a hydantoinase gene. The nucleotide sequence of the full-length hydantoinase gene is shown in SEQ ID NO:1, and its corresponding amino acid sequence is shown in SEQ ID NO:2. The resultant hydantoinase gene had 17% homology in amino acid sequence with a known hydantoinase gene derived from a microorganism of the genus *Pseudomonas* (J. Bacterial. 174, 962 (1992)). From this about 1.5-kb fragment, an about 40-bp sequence downstream from the hydantoinase gene was obtained, and this sequence was confirmed to have homology with a known N-carbamyl-L-amino acid hydrolase gene. Accordingly, it was attempted to obtain the full-length N-carbamyl-L-amino acid hydrolase gene.

5. Isolation of the N-carbamyl-L-amino Acid Hydrolase Gene from the Gene Library For acquisition of the N-carbamyl-L-amino acid hydrolase gene, Southern hybridization was carried out. By PCR where the chromosomal DNA from *Microbacterium liquefaciens* AJ3912 was used as the template while the oligonucleotides shown in Table 3 were used as primers, a fragment (a part of the hydantoinase gene; about 0.8 kb) was amplified and used as the probe. The amplified fragment was prepared at a concentration of about 50 ng/μl, and as the probe, 16 μl of this DNA solution was labeled with DIG by incubation at 37° C. for 24 hours according to a protocol of DIG High Prime.

TABLE 3

Primers used for preparation of the probe for acquisition of the N-carbamyl-L-amino acid hydrolase gene

| Primer No. | Sequence | |
|---|---|---|
| 18 | ACGCCGAGAACGAGATGCTCATCCAGAC GC | SEQ ID NO:9 |
| 45 | GGTCACGAACTGCCCGAACCCCT | SEQ ID NO:10 |

Using this labeled probe, Southern hybridization was carried out in the method mentioned above, whereby a band was detected at a position of about 3.4 kb in a BglII-cleaved product ((3) in FIG. 1). From the cleaved product, a fragment of about 3.4 kb was recovered and ligated to pUC18 to prepare a library (150 strains) of *E. coli* JM109. Then, colony hybridization was carried out in the manner described above, to select one positive clone.

The plasmid carried on the selected clone was prepared, and the nucleotide sequence of the inserted fragment was determined, and as a result, an about 1.2-kb ORF was present downstream from the hydantoinase gene, and estimated to be an N-carbamyl-L-amino acid hydrolase gene. The nucleotide sequence of the full-length N-carbamyl-L-amino acid hydrolase gene is shown in SEQ ID NO:3 in the Sequence Listing, and its corresponding amino acid sequence is shown in SEQ ID NO:4 in the Sequence Listing. The resultant N-carbamyl-L-amino acid hydrolase gene had 39% homology in amino acid sequence with a known N-carbamyl-L-amino acid hydrolase gene derived from the genus *Pseudomonas* (J. Bacterial. 174, 962 (1992)).

Example 2

Expression of the Hydantoinase Gene and N-carbamyl-L-amino Acid Hydrolase Gene in *E. coli*

1. Construction of an Expression Plasmid

To express the two genes in *E. coli*, plasmids pUCHH and pUCCH having the two genes ligated to a downstream region from a lac promoter in pUC18 were constructed in the following manner. First, each gene was amplified (the hydantoinase gene was amplified to nucleotide 29 downstream of the termination codon) by PCR where the chromosomal DNA in *Microbacterium liquefaciens* AJ3912 was used as the template while the oligonucleotides shown in Table 4 were used as primers. The amplified fragments were treated with EcoRI and BamHI, ligated to an EcoRI- and BaMHI-cleaved fragment of pUC18, and introduced into *E. coli* JM109. From ampicillin resistance strains, a strain having the desired plasmids were selected, and the plasmids were designated expression plasmids pUCHH and pUCCH respectively.

TABLE 4

Primers used in amplification of the hydantoinase gene and N-carbamyl-L-amino acid hydrolase gene

| Gene | Primer | | Sequence | |
|---|---|---|---|---|
| Hydantoinase | 5'-side | | CGCGAATTCCGAGAAGGAGCGCTGTCATGTTC | SEQ ID NO:11 |
| | | EcoRI | Initiation codon | |
| | 3-side | | CGCGGATCCGATGCGATCGGCCCGCGCCTG | SEQ ID NO:12 |
| | | BamHI | | |
| N-carbamyl-L-amino acid hydrolase | 5'-side | | CGCGAATTCGCGAGAGGGAGGTGTCGTCATGA CGCTG | SEQ ID NO:13 |
| | | EcoRI | Initiation codon | |
| | 3-side | | CGCGGATCCAACGTCACCGGTCAAGCGCCGTC ACGA | SEQ ID NO:14 |
| | | BamHI | Termination codon | |

2. Preparation of a Cell-Free Extract

E. coli transformant harboring pUCHH and E. coli transformant harboring pUCCH were seeded and cultured at 37° C. for 16 hours in LB medium containing 0.1 mg/ml ampicillin. 1 ml of this seed culture liquid was added in a 500-ml Sakaguchi flask containing 50 ml LB medium, and then cultured at 37° C. In 2.5 hours after culture was initiated, isopropyl-1-thio-β-D-galactopyranoside (IPTG) was add thereto at a final concentration of 1 mM, and culture was further continued for 4 hours.

After the culture was finished, the microorganism was collected, washed, suspended in 5 ml of 50 mM KPB (pH 8.0) and disrupted with 0.1 mmφ glass beads for 3 minutes (30 seconds×6 times at 90-second intervals) with a beads beater. The solution was recovered and centrifuged at 20,000 g×10 minutes, and the supernatant was used as the cell-free extract.

3. Measurement of the Activities of Hydantoinase and N-carbamyl-L-amino Acid Hydrolase For measurement of the hydantoinase activity, a reaction solution containing 120 mg/dl 5-benzyl hydantoin (BH; D-, L- and DL-hydantoin), 50 mM KPB (pH 8.0) and an enzyme solution was incubated at 37° C. for 30 minutes, then a 9-fold volume of 1.1 mM CuSO4 and 11.1 mM H3PO4 was added thereto and centrifuged at 20,000 g×10 minutes, to remove precipitates, and the formed N-carbamyl phenylalanine (N-Car-Phe) was quantified by HPLC to determine the hydantoinase activity. The enzyme activity causing formation of 1 μmol N-carbamyl phenylalanine per minute under these conditions was defined as 1 U of the enzyme activity.

For measurement of the N-carbamyl-L-amino acid hydrolase activity, a reaction solution containing 80 mg/dl N-carbamyl-L-phenylalanine, 50 mM KPB (pH7.5) and an enzyme solution was incubated at 37° C. for 30 minutes, then a 9-fold volume of 1.1 mM CuSO4 and 11.1 mM $H_3PO_4$ was added thereto and centrifuged at 20,000 g×10 minutes, to remove precipitates, and the formed L-phenylalanine (L-Phe) was quantified by HPLC to determine the N-carbamyl-L-amino acid hydrolase activity. The enzyme activity causing formation of 1 μmol L-phenylalanine per minute under these conditions was defined as 1 U of the enzyme activity.

The HPLC conditions used in measurement of the two enzymes are as follows:

Column: Daicel Chemical Industries Ltd. CHIRALPAK WH 0.46 cmφ×25 cm

Mobile phase: 5% (v/v) methanol, 1 mM CuSO4

Column temperature: 50° C.

Flow rate: 1.5 ml/min.

Detection: UV210

The results are shown in Table 5. In the strain transformed with pUCHH, a hydantoinase activity was detected, and in the strain transformed with pUCCH, an N-carbamyl-L-amino acid hydrolase activity was detected, and it was thus confirmed that the two genes are the hydantoinase gene and the N-carbamyl-L-amino acid hydrolase gene respectively derived from *Microbacterium liquefaciens* AJ3912, and expressed in the *E. coli* microorganisms. With respect to the hydantoinase activity, D- and L-N-carbamyl phenylalanine was formed respectively in the presence of D- and L-5-benzyl hydantoin as the substrate, thus revealing that the enzyme could act both D- and L-amino acid.

TABLE 5

Enzyme activity of the cell-free extract of *E. coli* harboring pUCHH and pUCCH

| Plasmid | Addition of IPTG | Hydantoinase activity (U/mg) | | N-carbamyl-L-amino acid hydrolase activity (U/mg) |
|---|---|---|---|---|
| pUCHH | + | DL | 0.11 | Not detected |
|  | + | D | 0.10 | Not detected |
|  | + | L | 0.13 | Not detected |
|  | − | DL | 0.01 | Not detected |
|  | − | D | 0.01 | Not detected |
|  | − | L | 0.02 | Not detected |
| pUCHH | + | DL | Not detected | 0.10 |
|  | − | DL | Not detected | 0.01 |
| pUC18 | + | DL | Not detected | Not detected |
|  | − | DL | Not detected | Not detected |

4. Production of L-phenylalanine from L-5-benzyl Hydantoin

Out of the cell-free extracts described above, 0.01 ml each of IPTG-added extracts showing higher hydantoinase and N-carbamyl-L-amino acid hydrolase activities respectively, 0.5 g/dl L-5-benzyl hydantoin and 0.1 M KPB (pH 7.5) were subjected to stationary reaction at 30° C. The reaction solution was sampled with time, and a 9-fold volume of 1.1 mM CuSO4 and 11.1 mM H3PO4 was added thereto and centrifuged at 20,000 g×10 minutes, to remove precipitates, and the formed L-phenylalanine was quantified by HPLC.

The results are shown in Table 6. As shown in this table, L-phenylalanine could be formed efficiently from L-5-benzyl hydantoin by using the cell-free extracts prepared from the *E. coli* expressing the hydantoinase gene and N-carbamyl-L-amino acid hydrolase gene.

TABLE 6

Production of L-phenylalanine from L-5-benzyl hydantoin

| Reaction time (hr) | L-BH (g/dl) | N-Car-L-Phe (g/dl) | L-Phe (g/dl) |
|---|---|---|---|
| 0 | 0.50 | 0.00 | 0.00 |
| 5 | 0.31 | 0.12 | 0.05 |
| 12 | 0.15 | 0.11 | 0.22 |
| 24 | 0.00 | 0.01 | 0.42 |

Example 3

Production of L-phenylalanine by using the Washed *E. coli* Microorganism 0.5 g/dl (26 mM) L-5-benzyl hydantoin, 0.1 M KPB (pH 7.5), 1 g/dl washed microorganism of JM109/pUCHH, and 1 g/dl washed microorganism of JM109/pUCCH were mixed and reacted at 30° C. The reaction solution was sample with time, and its centrifuged supernatant was analyzed by HPLC, whereby the formed L-phenylalanine was quantified.

The results are shown in Table 7. As shown in this table, L-phenylalanine could be formed efficiently from L-5-benzyl hydantoin by using the washed microorganisms of *E. coli* expressing the hydantoinase gene and N-carbamyl-L-amino acid hydrolase gene respectively.

TABLE 7

Production of L-phenylalanine by the washed microorganisms of *E. coli*

| Reaction time (hr) | L-BH (g/dl) | N-Car-L-Phe (g/dl) | L-Phe (g/dl) |
|---|---|---|---|
| 0 | 0.50 | 0.00 | 0.00 |
| 5 | 0.39 | 0.04 | 0.05 |
| 12 | 0.22 | 0.05 | 0.19 |
| 24 | 0.07 | 0.04 | 0.32 |
| 36 | 0.00 | 0.00 | 0.41 |

Example 4

Production of 2-amino-6-methyl-6-nitroheptanoic Acid by the Washed Microorganism of *E. coli*

100 mg L-5-(4-methyl-4-nitropentyl) hydantoin (MNPH) was suspended in 16 ml of 100 mM Tris-HCl buffer (pH 8.0), and 2 ml washed microorganism of JM109/pUCHH and 2 ml washed microorganism of JM109/pUCCH were added thereto and reacted at 37° C. The reaction solution was sample with time, and its centrifuged supernatant was analyzed by HPLC, whereby the formed 2-amino-6-methyl-6-nitroheptanoic acid (AMNHA) was quantified. The results are shown in Table 8. The HPLC conditions are as follows:

Column: GL Science Inert Sil ODS-20.46 cmφ×25 cm
Mobile phase: 30 mM aqueous phosphoric acid/methanol=8/2 (V/V)
Column temperature: 50° C.
Flow rate: 1.0 ml/min.
Detection: UV210 nm

TABLE 8

Production of 2-amino-6-methyl-6-nitroheptanoic acid by the washed microorganisms of *E. coli*

| Reaction time | Formed AMNHA (g/dl) | Remaining MNPH (g/dl) |
|---|---|---|
| 0 | 0.00 | 0.50 |
| 10 | 0.13 | 0.33 |
| 24 | 0.25 | 0.14 |
| 48 | 0.36 | 0.00 |

After the reaction, the reaction solution was diluted with 200 ml water, and the microorganisms were removed by centrifugation (12,000×g, 10 minutes). Thereafter, the supernatant was applied onto a cation-exchange resin column (Amberlite IR-120b, 2.6 cmφ×20 cm) at a flow rate of 3 ml/min., whereby 2-amino-6-methyl-6-nitroheptanoic acid was adsorbed thereon. The column was washed with 500 ml water, and 300 ml of 2% ammonia water was passed at a rate of 3 ml/min. through the column, to eluate 2-amino-6-methyl-6-nitroheptanoic acid. The eluate was concentrated to a volume of 3 ml under reduced pressure in a rotary evaporator at 40° C., followed by dropwise addition of acetone to give 2-amino-6-methyl-6-nitroheptanoic acid as an ammonium salt (dry salt: 31 mg). The resultant 2-amino-6-methyl-6-nitroheptanoic acid was subjected to HPLC analysis by an optical resolution column. The analysis conditions are as follows:

Column: Daicel Chemical Industries Ltd. CROWNPAK CR (+) 4.6 cmφ×25 cm
Mobile phase: Aqueous perchloric acid (pH 1.8)/acetonitrile=8/2 (V/V)
Column temperature: 50° C.
Flow rate: 1.0 ml/min.
Detection: UV210 nm Under these conditions, D-2-amino-6-methyl-6-nitroheptanoic acid and L-2-amino-6-methyl-6-nitroheptanoic acid can be fractionated and quantified at retention times of 4.2 and 6.1 minutes, respectively.

The result revealed that the 2-amino-6-methyl-6-nitroheptanoic acid formed in this reaction was in L-configuration, and its optical purity was 99% e.e. or more.

Example 5

Production of L-(3'-pyridyl)-alanine by the Washed Microorganisms of *E. coli*

100 mg L-5-(3'-pyridyl)-methyl hydantoin was suspended in 16 ml of 100 mM Tris-HCl buffer (pH 8.0), and 2 ml washed microorganism of JM109/pUCHH and 2 ml washed microorganism of JM109/pUCCH were added thereto and reacted at 37° C. for 48 hours. The reaction solution was centrifuged, and the supernatant was analyzed by HPLC, whereby the formed 3'-pyridyl-alanine was quantified. The HPLC conditions are as follows:

Column: Daicel Chemical Industries Ltd. CROWNPAK CR (+) 4.6 cmφ×25 cm
Mobile phase: Aqueous perchloric acid (pH 1.5)
Column temperature: 15° C.
Flow rate: 0.75 ml/min.
Detection: UV210 nm Under these conditions, D-(3'-pyridyl)-alanine and L-(3'-pyridyl)-alanine can be fractionated and quantified at retention times of 2.0 and 2.3 minutes, respectively.

The result revealed that 3'-pyridyl-alanine formed in this reaction was in L-configuration, and its optical purity was 99% e.e. or more. The amount of L-(3'-pyridyl)-alanine formed was 0.4 g/dl.

Example 6

Production of L-amino Acids by the Washed Microorganisms of *E. coli*

Various 5-substituted hydantoin compounds, 1 g/dl washed microorganism of JM109/pUCHH and 1 g/dl washed microorganism of JM109/pUCCH were mixed and reacted at 30° C. in the same manner as above in production of L-phenylalanine. After 24 hours, the reaction solution was sampled, and its centrifuged supernatant was analyzed by HPLC, whereby the formed L-amino acids were quantified.

The results are shown in Table 9. As shown in this table, L-amino acids could be formed efficiently from various 5-substituted hydantoin compounds by using the washed microorganisms of *E. coli* expressing the hydantoinase gene and N-carbamyl-L-amino acid hydrolase gene respectively.

TABLE 9

Production of L-amino acids by the washed microorganisms of *E. coli*

| 5-Substituted hydantoin compound | Formed amino acid | Amount of amino acid formed (g/dl) |
|---|---|---|
| L-5-benzyl hydantoin | L-phenylalanine | 0.32 |
| L-5-(4-hydroxybenzyl) hydantoin | L-tyrosine | 0.30 |

TABLE 9-continued

Production of L-amino acids by the washed microorganisms of *E. coli*

| 5-Substituted hydantoin compound | Formed amino acid | Amount of amino acid formed (g/dl) |
|---|---|---|
| L-5-indolyl methyl hydantoin | L-tryptophan | 0.41 |
| L-5-(3,4-dihydroxy benzyl) hydantoin | L-3,4-dihydroxy phenylalanine | 0.34 |
| L-5-methyl thioethyl hydantoin | L-methionine | 0.03 |

According to the present invention, the hydantoinase gene and N-carbamyl-L-amino acid hydrolase gene could be expressed stably in a large amount in a host such as colon bacteria. As a result, the enzymes could be easily prepared from such a transformant, and by using the transformant or its extract, or the purified enzymes etc., optically active amino acids useful for production of pharmaceutical preparations, products in chemical industry, food additives etc. could be efficiently produced.

INDUSTRIAL APPLICABILITY

As described above, the DNA encoding hydantoinase, the DNA encoding N-carbamyl-L-amino acid hydrolase, the recombinant DNA, the transformed cells, the method of producing a protein and the method of producing optically active amino acids according to the present invention are useful in fields related to production of optically active amino acids and used preferably in fields such as pharmaceutical preparations, products in chemical industry, food additives etc.

The invention claimed is:

1. An isolated protein having hydantoinase activity, wherein said protein has an amino acid sequence selected from the following amino acid sequence (c) or(d):
   (c) the amino acid sequence of SEQ ID NO:2, and
   (d) an amino acid sequence wherein in the amino acid sequence of SEQ ID NO:2, one to ten amino acid residues are replaced, deleted, inserted, or added.

2. The isolated protein according to claim 1, wherein the protein acts on at least DL-5-(4-hydroxybenzyl) hydantoin.

3. The isolated protein according to claim 1, wherein said protein has the amino acid sequence of SEQ ID NO: 2.

4. The isolated protein according to claim 1, wherein said protein has an amino acid sequence wherein in the amino acid sequence of SEQ ID NO:2, one to ten amino acid residues are replaced, deleted, inserted, or added.

5. A method for producing N-carbamylamino acids, comprising contacting a 5-substituted hydantoin with the protein of claim 3.

6. A method of producing optically active amino acids, comprising contacting a 5-substituted hydantoin with the protein of claim 3 and an enzyme optico-selectively hydrolyzing N-carbamylamino acids, wherein said enzyme optico-selectively hydrolyzing N-carbamylamino acids is an N-carbamyl-L-amino acid hydrolase encoded by SEQ ID NO: 3.

7. A method of producing optically active amino acids, comprising contacting a 5-substituted hydantoin with the protein of claim 3 and an enzyme optico-selectively hydrolyzing N-carbamylamino acids, wherein said enzyme optico-selectively hydrolyzing N-carbamylamino acids is an N-carbamyl-L-amino acid hydrolase having an amino acid sequence wherein in the amino acid sequence of SEQ ID NO:4, one to ten amino acid residues are replaced, deleted, inserted, or added.

8. A method of producing optically active tyrosine, comprising contacting DL-5-(4-hydroxybenzyl)hydantoin with: (a) the protein of claim 3, and (b) an enzyme optico-selectively hydrolyzing N-carbamylamino acids or a material containing the enzyme, wherein said enzyme optico-selectively hydrolyzing N-carbamylamino acids is an N-carbamyl-L-amino acid hydrolase encoded by SEQ ID NO: 3.

9. A method of producing optically active tyrosine, comprising contacting DL-5-(4-hydroxybenzyl)hydantoin with: (a) the protein of claim 3, and (b) an enzyme optico-selectively hydrolyzing N-carbamylamino acids or a material containing the enzyme, wherein said enzyme optico-selectively hydrolyzing N-carbamylamino acids is an N-carbamyl-L-amino acid hydrolase having an amino acid sequence wherein in the amino acid sequence of SEQ ID NO:4, one to ten amino acid residues are replaced, deleted, inserted, or added.

10. A method for producing N-carbamylamino acids, comprising contacting a 5-substituted hydantoin with the protein of claim 4.

11. A method of producing optically active amino acids, comprising contacting a 5-substituted hydantoin with the protein of claim 4 and an enzyme optico-selectively hydrolyzing N-carbamylamino acids, wherein said enzyme optico-selectively hydrolyzing N-carbamylamino acids is an N-carbamyl-L-amino acid hydrolase encoded by SEQ ID NO: 3.

12. A method of producing optically active amino acids, comprising contacting a 5-substituted hydantoin with the protein of claim 4 and an enzyme optico-selectively hydrolyzing N-carbamylamino acids, wherein said enzyme optico-selectively hydrolyzing N-carbamylamino acids is an N-carbamyl-L-amino acid hydrolase having an amino acid sequence wherein in the amino acid sequence of SEQ ID NO:4, one to ten amino acid residues are replaced, deleted, inserted, or added.

13. A method of producing optically active tyrosine, comprising contacting Dl-5-(4-hydroxybenzl)hydantion with: (a) the protein of claim 4, and (b) an enzyme, wherein said enzyme optico-selectively hydrolyzing N-carbamylamino acids or a material containing the enzyme, wherein said enzyme optico-selectively hydrolyzing N-carbamylamino acids is an N-carbamyl-L-amino acid hydrolase encoded by SEQ ID NO: 3.

14. A method of producing optically active tyrosine, comprising contacting DL-5-(4-hydroxybenzyl)hydantoin with: (a) the protein of claim 4, and (b) an enzyme optico-selectively hydrolyzing N-carbamylamino acids or a material containing the enzyme, wherein said enzyme optico-selectively hydrolyzing N-carbamylamino acids is an N-carbamyl-L-amino acid hydrolase having an amino acid sequence wherein in the amino acid sequence of SEQ ID NO:4, one to ten amino acid residues are replaced, deleted, inserted, or added.

* * * * *